(12) United States Patent
Chang et al.

(10) Patent No.: US 11,380,425 B2
(45) Date of Patent: Jul. 5, 2022

(54) ASSESSMENT AND MANAGEMENT SYSTEM FOR REHABILITATIVE CONDITIONS AND RELATED METHODS

(71) Applicant: REHABILITATION INSTITUTE OF CHICAGO, Chicago, IL (US)

(72) Inventors: Chih-Hung Chang, Chicago, IL (US); Andrew Bodine, Chicago, IL (US); James A. Sliwa, Chicago, IL (US)

(73) Assignee: REHABILITATION INSTITUTE OF CHICAGO, Chicago, IL (US)

( * ) Notice: Subject to any disclaimer, the term of this patent is extended or adjusted under 35 U.S.C. 154(b) by 0 days.

(21) Appl. No.: 16/142,313

(22) Filed: Sep. 26, 2018

(65) Prior Publication Data

US 2019/0096513 A1 Mar. 28, 2019

Related U.S. Application Data

(60) Provisional application No. 62/563,960, filed on Sep. 27, 2017.

(51) Int. Cl.
| | |
|---|---|
| *G16H 10/60* | (2018.01) |
| *G16H 10/20* | (2018.01) |
| *G16H 20/00* | (2018.01) |
| *G16H 50/30* | (2018.01) |
| *G16H 20/30* | (2018.01) |

(52) U.S. Cl.
CPC ............. *G16H 10/60* (2018.01); *G16H 10/20* (2018.01); *G16H 20/00* (2018.01); *G16H 50/30* (2018.01)

(58) Field of Classification Search
CPC ........ G16H 10/60; G16H 20/00; G16H 50/30; G16H 10/20; G16H 20/30
See application file for complete search history.

(56) References Cited

U.S. PATENT DOCUMENTS

| 8,463,623 | B2 | 6/2013 | Ware et al. | |
|---|---|---|---|---|
| 2006/0282306 | A1* | 12/2006 | Thissen-Roe | ........... G06Q 10/06 705/7.14 |
| 2009/0075246 | A1 | 3/2009 | Stevens | |
| 2009/0202969 | A1 | 8/2009 | Beauchamp et al. | |
| 2010/0191071 | A1 | 7/2010 | Anderson et al. | |
| 2012/0075586 | A1* | 3/2012 | Kirschen | ................ A61B 3/028 351/239 |
| 2012/0108909 | A1 | 5/2012 | Slobounov et al. | |
| 2013/0096942 | A1* | 4/2013 | Bowles | .................. G06Q 50/22 705/2 |

(Continued)

FOREIGN PATENT DOCUMENTS

JP 2005-228305 A 8/2005

OTHER PUBLICATIONS

Pathways to Success "Clinical Assessment Toolbox" Aug. 2016 (Year: 2016).*

(Continued)

*Primary Examiner* — Eliza A Lam

(74) *Attorney, Agent, or Firm* — Faegre Drinker Biddle & Reath LLP

(57) ABSTRACT

Systems and methods are disclosed for the measurement of patient outcomes in a rehabilitation setting. In one exemplary method, an assessment relating to self-care is provided, an assessment relating to mobility is provided, and an assessment relating to cognition is provided, wherein the assessments have been pre-selected using item response theory.

20 Claims, 7 Drawing Sheets

(56) References Cited

U.S. PATENT DOCUMENTS

| | | | |
|---|---|---|---|
| 2014/0081658 A1 | 3/2014 | Irving et al. | |
| 2014/0279727 A1 | 9/2014 | Baraniuk et al. | |
| 2016/0293036 A1* | 10/2016 | Niemi | G09B 7/04 |

OTHER PUBLICATIONS

Fabio La Porta et al. Unified Balance Scale: An activity-based, bed to community, and aetiology-independent measure of balance calibrated with Rasch analysisJ Rehabil Med 2011; 00: 00-00 (Year: 2011).*

PCT Search Report and Written Opinion issued in related application PCT/US2018/052875, dated Dec. 6, 2018, 7 pages.

Bjorner et al., "Developing tailored instruments: item banking and computerized adaptive assessment," Quality of Life Research, Feb. 15, 2007, vol. 16, pp. 95-108.

Cella et al., "A Discussion of Item Response Theory and Its Applications in Health Status Assessment," Medical Care, Sep. 2000, vol. 38(9), Suppl. II, pp. 66-72.

Cella et al., "Defining higher order dimensions of self-reported health: further evidence for a two-dimensional structure," Evaluation & The Health Professions, Jun. 2005, vol. 28(2), pp. 122-141.

Chang, "Finding Two Dimensions in MMPI-2 Depression," Structural Equation Modeling, 1996, vol. 3(1), pp. 41-49.

Chang et al., "Equating health-related quality of life instruments in applied oncology settings," Physical Medicine and Rehabilitations: State of the Art Reviews, 1997, vol. 11(2), pp. 397-406.

Chang et al., "Detecting Unexpected Variables in the MMPI-2 Social Introversion Scale," Journal of Applied Measurements, 2001, vol. 2(3), pp. 227-240.

Chang et al., "Real-Time Clinical Application of Quality-of-Life Assessment in Advanced Lung Cancer," Clinical Lung Cancer, Sep. 2002, vol. 4(2), pp. 104-109.

Chang et al., "Should symptoms be scaled for intensity, frequency, or both?" Palliative and Supportive Care, Mar. 2003, vol. 1(1), pp. 51-60.

Chang et al., "Psychometric evaluation of the Chicago Multiscale Depression Inventory in multiple sclerosis patients," Multiple Sclerosis, Mar. 2003, vol. 9(2), pp. 160-170.

Chang et al., "The Washington Psychosocial Seizure Inventory (WPSI): psychometric evaluation and future applications," Seizure, Jul. 2003, vol. 12(5), pp. 261-267.

Chang et al., "Item Response Theory and Its Applications to Patient-Reported Outcomes Measurement," Evaluation & The Health Professions, Sep. 2005, vol. 28(3), pp. 264-282.

Chang et al., "The SF-36 physical and mental health factors were confirmed in cancer and HIV/AIDS patients," Journal of Clinical Epidemiology, Jan. 2007, vol. 60(1), pp. 68-72.

Chang, "Patient-reported outcomes measurement and management with innovative methodologies and technologies," Quality of Life Research, May 26, 2007, vol. 16, pp. 157-166.

Chang et al., "A System for Interactive Assessment and Management in Palliative Care," Journal of Pain and Symptom Management, Jun. 2007, vol. 33(6), pp. 745-755.

Chang et al., "Psychometric evaluation of the Taiwan Chinese version of the EORTC QLQ-PR25 for HRQOL assessment in prostate cancer patients," Health and Quality of Life Outcomes, Aug. 2012, vol. 10:96, 10 pages.

Edwards, "An Overview of Item Response Theory," Vector Psychometric Group, Sep. 2014, <https://www.vpgcentral.com/wp-content/uploads/2014/10/VPG-DIA-9.21.14.pdf>, 50 pages.

Gehlert et al., "Establishing the Diagnostic Validity of Premenstrual Dysphoric Disorder Using Rasch Analysis," Journal of Outcome Measurement, 1997, vol. 1(1), pp. 2-18.

Gehlert et al., "Factor Structure and Dimensionality of the Multidimensional Health Locus of Control Scales in Measuring Adults with Epilepsy," Journal of Outcome Measurement, 1998, vol. 2(3), pp. 173-190.

Gehlert et al., "The WOMQOL instrument measured quality of life in women of reproductive age with no known pathology," Journal of Clinical Epidemiology, May 2006, vol. 59(5), pp. 525-533.

Leonelli et al., "Interpretation of a Full-Information Item-Level Factor Analysis of the MMPI-2: Normative Sampling and Nonpathognomonic Descriptors," Journal of Personality Assessment, Jun. 2000, vol. 74(3), pp. 400-422.

Liang et al., "An empirical comparison of the WHOQOL-BREF and the SGRQ among patients with COPD," Quality of Life Research, 2008, vol. 17, pp. 793-800.

Lin et al., "Development of a real-time clinical decision support system upon the web mvc-based architecture for prostate cancer treatment," BMC Medical Informatics and Decision Making, 2011, vol. 11(1): 16, 11 pages.

Lin et al., "A real time online assessment system with modelized architecture on clinical infometrics for patient reported outcomes of prostate cancer," Computer Methods and Programs in Biomedicine, Jun. 2012, vol. 106(3), pp. 249-259.

Muthen et al., "Examples: Confirmatory Factor Analysis and Structure Equation Modeling," Mplus User's Guide, Seventh Edition, Chapter 5, Sep. 2012, Los Angeles, CA, US, pp. 55-110.

Richards et al., "Palliative Care Symptom Assessment for Patients with Cancer in the Emergency Department: Validation of the Screen for Palliative and End-of-Life Care Needs in the Emergency Department Instrument," Journal of Palliative Medicine, Jun. 2011, vol. 14(6), pp. 757-764.

Snyder et al., "Can Patient-Reported Outcome Measures Identify Cancer Patients' Most Bothersome Issues?" Journal of Clinical Oncology, Mar. 20, 2011, vol. 29(9), pp. 1216-1220.

Snyder et al., "Feasibility and Value of Patient Viewpoint: A Web System for Patient-Reported Outcomes Assessment in Clinical Practice," Psychooncology, Apr. 2013, vol. 22(4), pp. 895-901.

Thissen et al., "Methodological issues for building item banks and computerized adaptive scales," Quality of Life Research, 2007, vol. 16, pp. 109-119.

Wolf et al., Development and validation of the Communication and Attitudinal Self-Efficacy scale for cancer (CASE-cancer), Patient Education and Counseling, Jun. 2005, vol. 57(3), pp. 333-341.

Zheng et al., "Content-balancing strategy in bifactor computerized adaptive patient-reported outcome measurement," Quality of Life Research, Apr. 2013, vol. 22(3), pp. 491-499.

Examination Report issued in related application AU 2018342443, dated Nov. 3, 2021, 5 pages.

Reigart, "Why Standardized Tests are so Important," May 12, 2017, retrieved from internet at <https://fprehab.com/2017/05/12/why-standardized-tests-are-so-important/> on Feb. 23, 2021, 3 pages.

Examination Report issued in related application AU 2018342443, dated Feb. 9, 2021, 6 pages.

Office Action issued in related application JP 2020-517303, dated Mar. 30, 2021, with English language translation, 7 pages.

Anonymous, "Electronic health record," Wikipedia, Aug. 31, 2017, retrieved from Internet: https://en.wikipedia.org/w/index.php?title=Electronic_health_record&oldid=798111921 on May 14, 2021, 44 pages.

Anonymous, "Rasch Model," Wikipedia, Jun. 7, 2017, retrieved from Internet: https://en.wikipedia.org/w/index.php?title+Rasch_Model&oldid=784244967 on May 14, 2021, 11 pages.

Haley et al., "Activity Outcome Measurement for Postacute Care," Medical Care, Jan. 1, 2004, vol. 42(1), pp. I-49-I-61.

Haley et al., "Computerized Adaptive Testing for Follow-Up After Discharge From Inpatient Rehabilitation: I. Activity Outcomes," Archives of Physical Medicine and Rehabilitation, Elsevier, Amsterdam, NL, Jul. 28, 2006, vol. 87(8) pp. 1033-1042.

World Health Organization, "International Classification of Functioning Disability and Health (ICF)," Dec. 31, 2001, retrieved from Internet: https://apps.who.int/iris/bitstream/handle/10665/42407/9241545429.pdf on May 14, 2021, 315 pages.

Office Action issued in related application CA 3,076,219, dated Apr. 30, 2021, 7 pages.

Extended European Search Report and Search Opinion issued in related application EP 18861460.6, dated May 26, 2021, 12 pages.

\* cited by examiner

Self Care

Eating
- ☐ 7- Complete Independence
- ☐ 6- Modified Independence
- ☐ 5- Supervision
- ■ 4- Minimal Assistance
- ☐ 3- Moderate Assistance
- ☐ 2- Maximal Assistance
- ☐ 1- Total Assistance
- ☐ 0- Not Observed

Grooming
- ☐ 7- Complete Independence
- ☐ 6- Modified Independence
- ☐ 5- Supervision
- ■ 4- Minimal Assistance
- ☐ 3- Moderate Assistance
- ☐ 2- Maximal Assistance
- ☐ 1- Total Assistance
- ☐ 0- Not Observed

Bathing
- ☐ 7- Complete Independence
- ☐ 6- Modified Independence
- ☐ 5- Supervision
- ■ 4- Minimal Assistance
- ☐ 3- Moderate Assistance
- ☐ 2- Maximal Assistance
- ☐ 1- Total Assistance
- ☐ 0- Not Observed

Mobility

Bed/Chair Transfer
- ☐ 7- Complete Independence
- ☐ 6- Modified Independence
- ☐ 5- Supervision
- ☐ 4- Minimal Assistance
- ☐ 3- Moderate Assistance
- ☐ 2- Maximal Assistance
- ☐ 1- Total Assistance
- ■ 0- Not Observed

Tub/Shower Transfer
- ☐ 7- Complete Independence
- ☐ 6- Modified Independence
- ☐ 5- Supervision
- ☐ 4- Minimal Assistance
- ☐ 3- Moderate Assistance
- ☐ 2- Maximal Assistance
- ☐ 1- Total Assistance
- ■ 0- Not Observed

Toilet Transfer
- ☐ 7- Complete Independence
- ☐ 6- Modified Independence
- ☐ 5- Supervision
- ☐ 4- Minimal Assistance
- ☐ 3- Moderate Assistance
- ☐ 2- Maximal Assistance
- ☐ 1- Total Assistance
- ■ 0- Not Observed

| FIG. 6A | FIG. 6B |

FIG. 6A

Upper Body Dressing

☐ 7- Complete Independence
☐ 6- Modified Independence
☐ 5- Supervision
■ 4- Minimal Assistance
☐ 3- Moderate Assistance
☐ 2- Maximal Assistance
☐ 1- Total Assistance
☐ 0- Not Observed

Lower Body Dressing

☐ 7- Complete Independence
☐ 6- Modified Independence
☐ 5- Supervision
■ 4- Minimal Assistance
☐ 3- Moderate Assistance
☐ 2- Maximal Assistance
☐ 1- Total Assistance
☐ 0- Not Observed

Toileting

☐ 7- Complete Independence
☐ 6- Modified Independence
☐ 5- Supervision
■ 4- Minimal Assistance
☐ 3- Moderate Assistance
☐ 2- Maximal Assistance
☐ 1- Total Assistance
☐ 0- Not Observed

Locomotion-Walk

☐ 7- Complete Independence
☐ 6- Modified Independence
☐ 5- Supervision
☐ 4- Minimal Assistance
☐ 3- Moderate Assistance
☐ 2- Maximal Assistance
☐ 1- Total Assistance
■ 0- Not Observed

Locomotion-Wheelchair

☐ 7- Complete Independence
☐ 6- Modified Independence
☐ 5- Supervision
☐ 4- Minimal Assistance
☐ 3- Moderate Assistance
☐ 2- Maximal Assistance
☐ 1- Total Assistance
■ 0- Not Observed

Locomotion-Stairs

☐ 7- Complete Independence
☐ 6- Modified Independence
☐ 5- Supervision
☐ 4- Minimal Assistance
☐ 3- Moderate Assistance
☐ 2- Maximal Assistance
☐ 1- Total Assistance
■ 0- Not Observed

| FIG. 6A | FIG. 6B |

FIG. 6B

☐ 5- Supervision or Setup    ☐ 5- Supervision or Setup
☐ 4- Minimal Contact Assistance    ☐ 4- Minimal Contact Assistance
☐ 3- Moderate Assistance    ☐ 3- Moderate Assistance
☐ 2- Maximal Assistance    ☐ 2- Maximal Assistance
☐ 1- Total Assistance    ☐ 1- Total Assistance
■ 0- Not Observed    ■ 0- Not Observed ☐ 5- Supervision or Setup    ☐ 5- Supervision or Setup
☐ 4- Minimal Contact Assistance    ☐ 4- Minimal Contact Assistance
☐ 3- Moderate Assistance    ☐ 3- Moderate Assistance
☐ 2- Maximal Assistance    ☐ 2- Maximal Assistance
☐ 1- Total Assistance    ☐ 1- Total Assistance
■ 0- Not Observed    ■ 0- Not Observed ☐ 5- Supervision or Setup
☐ 4- Minimal Contact Assistance
☐ 3- Moderate Assistance
☐ 2- Maximal Assistance
☐ 1- Total Assistance
■ 0- Not Observed Self Care eatingC
groomingC
bathingC
dressingUpperC
dressingLowerC
toiletingC

-2 -1 0 1 2 3

Mobility

3%
2%
1%
0% ··· Please enter Mobility goals
-1%
-2%
-3%
0   0.2   0.4   0.6   0.8   1

Cognition 3
2
1
0 ··· Please enter Cognition goals
-1
-2
-3
0   0.2   0.4   0.6   0.8   1

FIG. 7

ASSESSMENT AND MANAGEMENT SYSTEM FOR REHABILITATIVE CONDITIONS AND RELATED METHODS

CROSS-REFERENCE TO RELATED APPLICATIONS

The present application claims the priority benefit of U.S. Provisional Patent Application 62/563,960, filed Sep. 27, 2017, which is incorporated herein by reference in its entirety.

TECHNICAL FIELD

The present disclosure relates generally rehabilitative techniques and, more particularly, to a computer-assisted method for assessing a patient.

BACKGROUND

An "outcomes measure," also known as an "outcomes assessment tool," is a series of items used to determine varying medical conditions or functional status of a patient. One outcomes measure is the Functional Independence Measure (FIM®), which provides a method of measuring functional status. The assessment contains eighteen items composed of motor tasks (13 items) and cognitive tasks (5 items). Tasks are rated by a clinician on a seven-point ordinal scale that ranges from total assistance to complete independence. Scores range from 7 (lowest) to 91 (highest) for motor skills and 7 to 35 for cognition skills. Items include eating, grooming, bathing, upper body dressing, lower body dressing, toileting, bladder management, bowel management, bed to chair transfer, toilet transfer, shower transfer, locomotion (ambulatory or wheelchair level), stairs, cognitive comprehension, expression, social interaction, problem solving, and memory.

The FIM measure uses a scoring criteria that ranges from a score of 1 (which reflects total assistance) to a score of 7 (which reflects complete independence). A score of 7 is intended to reflect that a patient has complete independence. A score of 1 is intended to reflect that a patient can perform less than 25% of the task or requires more than one person to assist. As a result of this scoring system, many patients who make improvements in a free-standing inpatient rehabilitation facility or an inpatient rehabilitation unit within a hospital do not necessarily register gains in their outcomes score during their rehabilitation. For instance, a spinal cord injury patient may make significant improvements to fine finger skill motor skills during rehabilitation, allowing the patient to use a computer or a smart phone. However, his or her FIM score in this situation would not improve.

An outcomes measure is needed that more accurately captures assessment of a patient's medical condition or functional status. Additionally, an outcomes measure is needed that helps to better identify areas in which patients, such as rehabilitation patients, can improve.

An "item" is a question or other kind of assessment used in an outcomes measure. For example, one item on an outcomes measure known as the Berg Balance Scale instructs a patient as follows: "Please stand up. Try not to use your hands for support." A "rating" is a score outcome or other evaluation in response to an item assessment. For example, the ratings for the Berg Balance Scale item are as follows: a rating of 4, which reflects that the patient is able to stand without using her hands and stabilize independently; a rating of 3, which reflects that the patient is able to stand independently using her hands; a rating of 2, which reflects that the patient is able to stand using her hands after several tries; a rating of 1, which reflects that the patient needs minimal aid from another to stand or to stabilize; and a rating of 0, which reflects that the patient needs moderate or maximal assistance from another to stand.

Classical test theory is a body of related psychometric theory that predicts outcomes of educational assessment and psychological testing such as the difficulty of items or the ability of test-takers. It is a theory of testing based on the idea that a person's observed or obtained score on a test is the sum of a true score (error-free score) and an error score. Classical test theory assumes that each person has a true score, T, that would be obtained if there were no errors in measurement. A person's true score is defined as the expected number-correct score over an infinite number of independent administrations of the test. Unfortunately, test users never observe a person's true score, only an observed score, X. It is assumed that observed score=true score plus some error, or $X=T+E$, where X is the observed score, T is the true score, and E is the error. The reliability, i.e., the overall consistency of a measure, of the observed test score X is defined as the ratio of true score variance to the observed score variance. Because the variance of the observed scores can be shown to equal the sum of the variance of true scores and the variance of error scores, this formulates a signal-to-noise ratio wherein reliability of test scores becomes higher as the proportion of error variance in the test scores becomes lower and vice versa. The reliability is equal to the proportion of the variance in the test scores that could be explained if the true scores were known. The square root of the reliability is the correlation between true and observed scores. Estimates of reliability can be obtained by various means, such as the parallel test or a measure of internal consistency known as Cronbach's coefficient $\alpha$. Cronbach's $\alpha$ can be shown to provide a lower bound for reliability, and thus, the reliability of test scores in a population is always higher than the value of Cronbach's $\alpha$ in that population.

SUMMARY

The problem of accurately measuring improvements in rehabilitation patients is solved by developing an outcomes assessment that incorporates factor analysis and item response theory.

The problem of measuring improvements in rehabilitation patients is solved by asking a series of questions to the patient and returning a domain-specific and/or composite score.

The problem of improving care in rehabilitation patients is solved by predicting the domain-specific and/or composite score on an outcomes measurement of the patient and providing a clinical intervention if the domain-specific and/or composite score falls below the predicted score.

DRAWINGS

While the appended claims set forth the features of the present techniques with particularity, these techniques, together with their objects and advantages, may be best understood from the following detailed description taken in conjunction with the accompanying drawings of which:

FIG. 1 displays a flowchart for certain exemplary methods for preparing a preliminary outcomes measure;

FIG. 2 displays a flowchart for electronically collecting ratings for the items in the preliminary outcomes measure;

FIG. 3 displays an exemplary scoring system of the IRT, comparing it against a FIM® score known in the prior art;

FIG. 4 displays an exemplary plot of certain data relating to patient scores in the Self Care, Cognition, and Mobility domains;

FIG. 5 further shows a patient's current and expected functional status on each of the items/tasks in the Self Care domain;

FIG. 6A and FIG. 6B are an "FIM Explorer" section, with features to allow clinicians to select and/or set the goal for each FIM-specific task;

FIG. 7 shows a comparison chart; and

Figure 8:
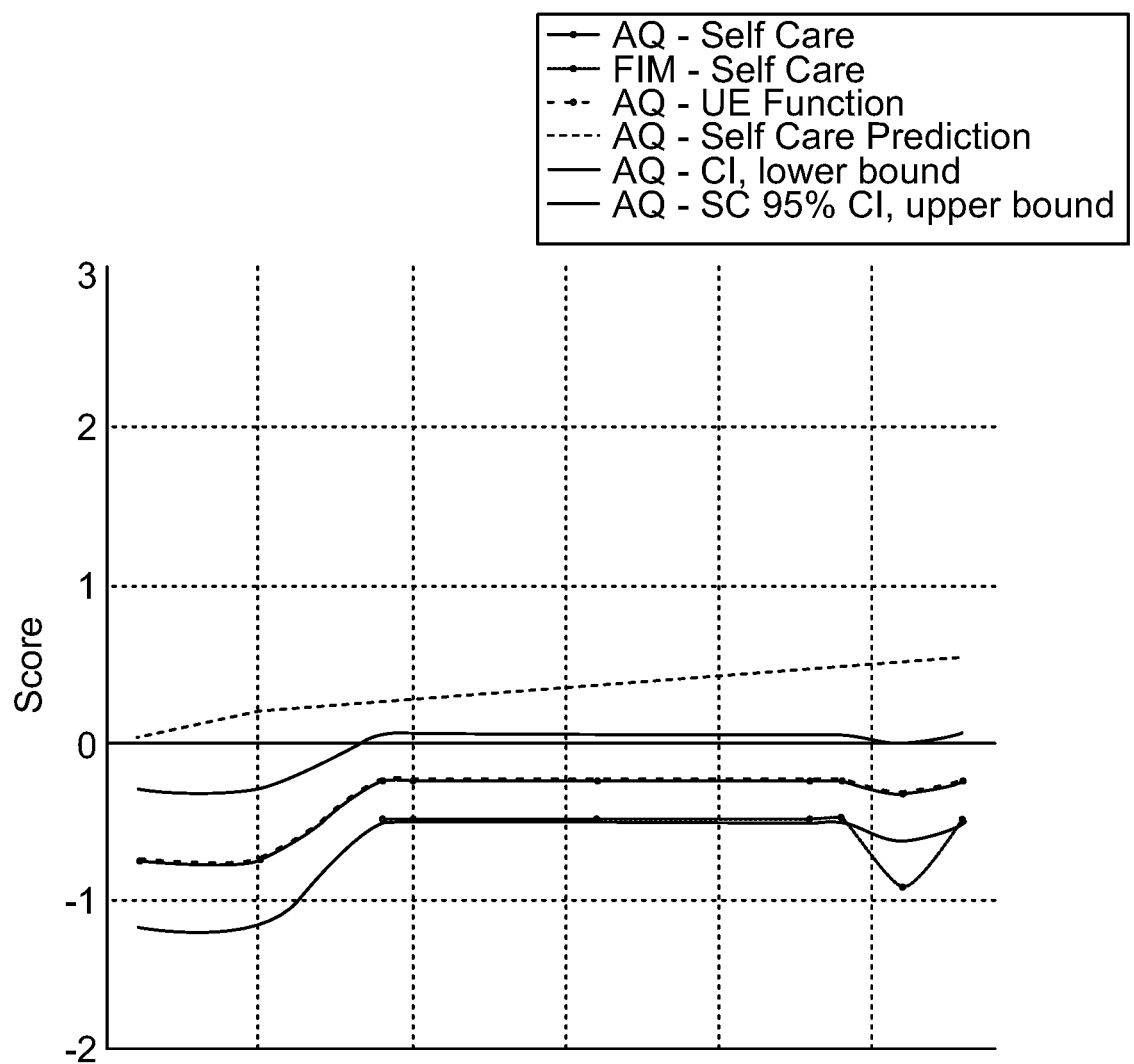

FIG. 8 displays various plots for the Self Care domain in comparison with a patient's FIM score.

DETAILED DESCRIPTION

A "bifactor model" is a structural model wherein items cluster onto a specific factors while at the same time loading onto a general factor.

The term "categorical" is used to describe response options for which there is no explicit or implied order or ranking.

A "Comparative Fit Index" (CFI) compares the performance of the constructed structural model against the performance of a model that postulates no relationships between variables. A good-fitting model generally has a CFI greater than 0.95.

A "complex structure" is a CFA structural model where at least one item loads onto more than one factor.

"Confirmatory factor analysis" (CFA) is a form of factor analysis utilized where a psychometrician has an understanding of how the latent traits and items should be grouped and related. A structural model is developed, and this is fit to the data. A goal of the model is to achieve a good fit with the data.

A "constraint" is a restriction imposed on a model for the sake of mathematical stability or the application of content area theory. For example, if two factors in a confirmatory factor analysis are not expected to have any relationship between them, a constraint on that correlation (requiring that it equal 0.00) can be added to the model.

A "continuous" variable is a variable that is measured without categories, like time, height, weight, etc.

A "covariate" is a variable in a model that is not on a measure, but may still have some explanatory power. For example, in rehabilitation research, it may occasionally be useful to include covariates for age, sex, length of stay, diagnostic group, etc.

"Dichotomous" describes response options that are ordinal with two categories (e.g., low versus high). Alternatively, it may refer to items that are scored correct vs. incorrect, which are conceptually also ordinal responses with two categories.

"Differential item functioning" (DIF), in item response theory, is a measure of how the parameter estimates may behave differently from group to group (in different samples) or from observation to observation (over time).

"Difficulty," in item response theory, is the required minimum level of a latent trait that is necessary to respond in a certain way. On a measure with dichotomous responses, there is a single difficulty (e.g., the minimum level of the latent trait that will raise the probability of answering correctly to 50% or greater). On a measure with polytomous responses, "difficulty" is better described as "severity," as there is not usually a correct or incorrect answer. On a measure with polytomous responses, the number of difficulties estimated is k−1, where k is the number of response options. These difficulties describe the level of latent trait necessary to endorse the next highest category. Sometimes also referred to as a threshold.

"Dimension" refers to the number of latent traits a measure addresses. A measure that records one trait is said to be unidimensional, while a measure recording more than one trait is referred to as multidimensional.

"Discrimination" is the ability of a test to differentiate between people with high versus low ability of the latent trait. Similarly, it describes the magnitude of the relationship between an item and a latent trait. Conceptually, it is very similar to a factor loading and mathematically, it can be converted into a factor loading.

"Endorse" means to select a response option.

"Equality constraint" in item response theory and confirmatory factor analysis, is a mathematical requirement to constrain the discriminations or factor loadings to be equal when only two items load onto a factor.

"Equating" refers to the use of item response theory to draw similarities between the scores on different measures that record the level of the same latent trait(s). Equating may also be used to compare alternate forms of the same measure.

"Error" refers to a term to describe the amount of uncertainty surrounding a model. A model with parameter estimates that are very close to the observed data will have low amounts of error, while one that is quite different would have a large amount of error. Error may also indicate the amount of uncertainty surrounding a specific parameter estimate itself.

"Estimation" refers to the statistical process of deriving parameter estimates from the data. These procedures may be performed using specialized psychometric software known in the art.

"Exploratory factor analysis" is a form of factor analysis that clusters items according to their correlations. This is often done without any direction from the analyst other than how many factors should be extracted. The groupings are then "rotated." Rotation methods attempt to find factor loadings that are indicative of simple structure by making sure that factor loadings are pushed towards −1.00, 0.00, or 1.00.

"Factor" in factor analysis describes a latent trait. Unlike a latent trait in item response theory, factors do not normally have scores associated with them.

"Factor analysis" is a statistical method for determining the strength and direction of the relationships between factors and items. The data on which factor analysis is based are the correlations between items. Factor analysis can accommodate either ordinal or continuous data, but not unordered categorical. It is possible to compute scores from factor analysis, but IRT scores are more reliable. May either be exploratory or confirmatory.

"Factor correlation" refers to a correlation between two factors. A CFA model with correlated factors is called "oblique."

"Factor loading," in factor analysis, describes the magnitude of the relationship between an item and a factor. It is not mathematically the same as a correlation, though its scale and interpretation are similar. That is, values (usually) range from −1.00 to 1.00. A strong negative factor loading indicates a strong inverse relationship between an item and a latent trait, while a strong positive loading has the opposite interpretation. A factor loading of 0.00 indicates no relationship whatsoever.

"Fit statistics" or "fit index" refer to metrics used to quantify how well the model performs. Popular fit metrics confirmatory factor analysis and structural equation modeling include the root mean square error of approximation (RMSEA), the comparative fit index (CFI), the Tucker-Lewis Index (TLI), and the weighted root mean-square residual/standardized root mean-square residual (WRMR/SRMR).

"General factor," in a bifactor model, refers to the factor onto which all items load.

"Graded response model" (GRM) is an extension of the two-parameter logistic model that allows for ordinal responses. Instead of only one difficulty, the graded response model yields k−1 difficulties, where k is the number of response categories.

"Hierarchical model" is a structural model where latent traits load onto other latent traits, forming a hierarchy.

"Higher-/lower-order factor," in a hierarchical model, is a higher-order factor is a type of latent variable onto which lower-order factors load.

"Index" is a term used to refer to a fit index/statistic (e.g., comparative fit index) or as a synonym for "measure."

"Item" refers to the questions, tasks, or ratings on a measure that are addressed by a respondent or a respondent's representative (such as a clinician).

"Item characteristic curve (ICC)" is a graph that plots the probability of selecting different response options given the level of a latent trait. Sometimes it also is called a "trace line."

"Item response theory" (IRT) is a collection of statistical models used to obtain scores and determine item behavior according to a structural model. In one used form, IRT uses the response pattern of every person in the sample in order to get these item and score estimates. IRT uses data that are ordinal or categorical. Mathematically speaking, item response theory uses item and person characteristics in order to predict the probability that a person selects a certain response option on a given item.

"IRT score" is a score specific to IRT analysis that is given on a standardized scale. It is similar to a z-score. In one IRT scoring system, a score of 0.00 implies someone has an average level of a latent trait, a large negative score implies a low level of the latent trait, and a large positive value implies a large level of a latent trait.

"Latent trait" is similar to a factor in factor analysis, but used more often in item response theory. A latent trait is what a related set of items purports to measure. It may be used interchangeably with factor, domain, or dimension.

"Latent variable" is a term for a variable that is not measured directly. It includes latent traits.

"Linking" is similar to equating, but for item parameter estimates rather than scores.

"Load" is a verb used to describe what an item does on a factor. For example: "Item 4 loads onto the both the local dependence factor as well as the general factor in this model."

"Local dependence" (LD) is a violation of the local independence assumption in which items are related for some reason other than the latent trait. If local dependence appears to exist in the data, it can be accounted for by either modeling a correlation between the items or by creating a local dependence factor. This can be due to a large number of reasons, such as similar wording, nearly identical content, and the location of the items on a measure (this last example occurs frequently on the last items of a long measure).

"Local independence" refers to an assumption in psychometrics that states that the behavior of items is due to the latent traits in the model and item-specific error and nothing else. When items violate this assumption, they are said to be locally dependent.

"Manifest variable" is a generic term for a variable that is measured directly, and includes items, covariates, and other such variables.

"Measure" or "measurement" refers to a collection of items that attempt to measure the level of some latent trait. It may be used interchangeably with assessment, test, questionnaire, index, or scale.

"Model" in psychometrics is a combination of the response model and the structural model. In general terms, it describes both the format of the data and how the data recorded in the model's variables should be related.

"Model fit" is a term used to describe how well a model describes the data. This may be done in a variety of ways, such as comparing the observed data against the predictions made by the model or comparing the chosen model against a null model (a model in which none of the variables are related). The metrics used to assess model fit are called fit statistics.

"Multidimensional" is a term used to describe a measure that records more than one latent trait.

"Multigroup analysis" in IRT refers to the process by which the sample can be split into different groups, and parameter estimates specific to each group may be estimated.

"Nominal model" is similar to the graded response model, but for items with response options that are categorical rather than ordinal.

"Oblique" is an adjective used to describe factors that are correlated.

"Ordinal" describes the way an item records data. For example, possible responses to an item are a series of categories ordered from low to high or high to low.

"Orthogonal" describes factors that are restricted to a zero correlation.

"Parameter estimate" is a statistically-derived value estimated by psychometric software. It is a generic term that may include things like item discriminations, factor loadings, or factor correlations.

"Path diagram" is a diagram meant to illustrate the relationships between items, latent traits, and covariates. In a path diagram, rectangles/squares represent observed variables (i.e., items, covariates, or any modeled variable for which there is explicitly recorded information), ovals/circles represent latent traits or variables for which there is no explicitly recorded information, one-headed arrows reflect one-directional relationships (as in a regression), and two-headed arrows reflect correlation/covariance between modeled variables.

"Polytomous" is a term for items with more than one response option, and may be either ordinal or categorical.

"Pseudobifactor model" is a bifactor model where not all items cluster onto specific factors. Instead, some items may only load onto the general factor.

"Psychometrician" is a kind of statistician that specializes in measurement.

"Psychometrics" describes the statistics used in creating or describing measures.

"Rasch model" is a response model that hypothesizes that all item discriminations are equal to 1.00. It usually is not used unless this assumption is true or nearly true. This assumption eases interpretation of scores and difficulties and allows use of item response theory on (relatively) small sample sizes, but it is very uncommon that all item discriminations behave identically. It is a simplified case of the two-parameter logistic model, which allows the item discriminations to vary. Because of this, the Rasch model is sometimes referred to as the one-parameter logistic model (1PL). It may be used when the responses are dichotomous.

A "respondent" is someone who answers items on a measurement.

A "response" is a respondent's answer to an item.

"Response categories" are the different options a respondent may select as a response to an item. If items yield dichotomous responses, the data are recorded as either correct (1) or incorrect (0).

"Response model," in item response theory, refers to the way a measurement model handles the format of the responses. Popular response models include the Rasch model, the two-parameter logistic model, the three-parameter logistic model, the graded response model, and the nominal model.

A "response pattern" is a series of numbers representing a respondent's answers to each question on a measurement.

"Root mean square error of approximation" (RMSEA) is a fit statistic in applied psychometrics. It measures the closeness of the expected data (the data that the model would produce) against the observed data. It is usually desirable that the RMSEA is below 0.08, though some of ordinary skill in the art desire that the RMSEA be below 0.05.

A "score" is a numeric value meant to represent the level or amount of the latent trait a respondent possesses. Classical test theory computes scores as the sum of item responses, while item response theory estimates these using both response patterns and item qualities.

"Sigmoid" (literally, "S-shaped") is an adjective is occasionally used to describe the shape of the TCC or the ICC of a 2PL item.

"Simple structure" is a structural model where all items load onto one factor at a time.

"Specific factor," in a bifactor model, is a factor onto which a set of items load.

"Structural equation modeling" (SEM) is an extension of confirmatory factor analysis (CFA) that allows relationships between latent variables like latent traits. If all latent variables in the model are latent traits, structural equation modeling (SEM) and CFA are often used interchangeably.

"Structural model" is a mathematical description that represents a system of hypotheses regarding the relationships between latent traits and items. It is depicted as a path diagram.

"Sum score" is a score computed by summing the numeric value of all responses on a measure.

"Sum score conversion" (SSC) is a table that shows the relationship between the sum scores and an IRT scores.

"Test characteristic curve" (TCC) is a figure that plots the relationship between sum scores and IRT scores.

"Testlet" is a small collection of items that measure some component of the overall latent trait. Creating a measure comprised of testlets can lead to more easily interpreted scores when the definition of the latent trait is clearly defined beforehand.

"Threshold": see "difficulty".

"Tucker-Lewis Index" (TLI) is a fit index that compares the performance of the constructed model against the performance of a model that postulates no relationships between the variables. A good fitting model usually has a TLI of greater than 0.95.

"Three-parameter logistic model" (3PL) is an extension of the two-parameter logistic model that also includes a "guessing" parameter. For example, in a multiple-choice item with 4 choices, even guessing randomly results in a 25% chance of answering correctly. The 3PL allows for this non-zero chance of answering correctly. It is used when responses are dichotomous.

"Trace line": see "item characteristic curve."

"Two-parameter logistic model" (2PL) is like the Rasch Model, but allows item discriminations to vary. It may be used when item responses are dichotomous.

"Unidimensional" is a term used to describe a measure that records only one latent trait.

"Variable" is a generic word used to describe a set of directly (manifest) or indirectly (latent) recorded data that measures a single thing.

"Weighted root mean-square error/standardized root mean-square error" (WRMR/SRMR) is a fit statistic that measures the magnitude of a model's residuals. Residuals are the differences between the observed data and the data that the model predicts. The typical recommended WRMR value is below 1.00, though this recommendation may change based on size of the sample or complexity of the model. The WRMR is used when there is at least one categorical variable in the model, while the SRMR is used when all variables are continuous.

Figure 1:
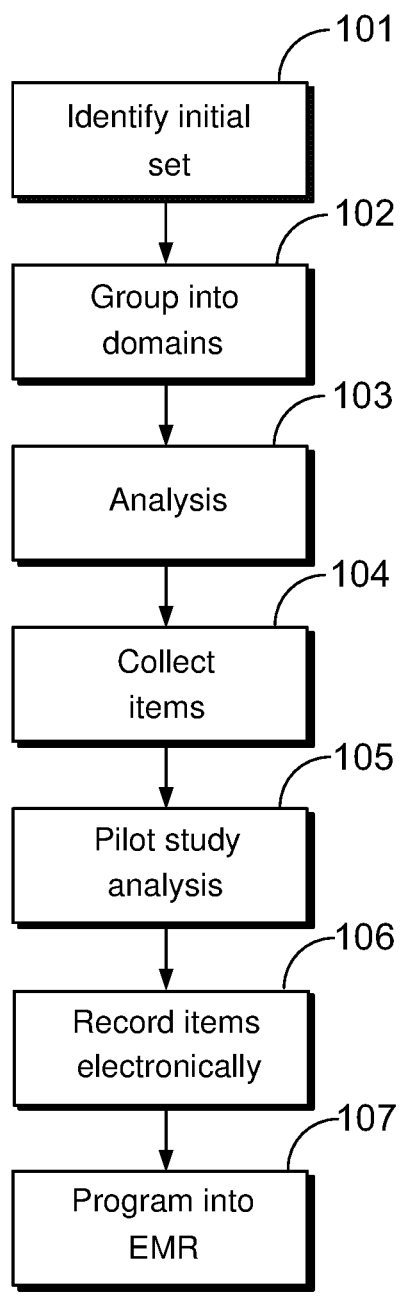

FIG. 1 displays a flowchart for certain exemplary methods for preparing a preliminary outcomes measure 100 for inclusion into an electronic medical record.

In 101, an item set 200 is identified. In an embodiment, clinicians may be queried to provide their input on appropriate items to include in the item set 200, based on their training, education, and experience. Examples of clinicians may include physicians, physical therapists, occupational therapists, speech language pathologists, nurses, and PCTs. Items from the item set 200 may come from a variety of outcomes measures known in the art.

In 102, the items from the item set 200 may be grouped into one or more of a plurality of areas, called "domains", that are relevant to therapy or clinical outcomes. The clinicians may identify these domains. In an embodiment, items from the item set 200 may be grouped into three domains, titled "Self-Care", "Mobility", and "Cognition". It should be understood that other groupings of additional and/or alternative domains are possible.

In 103, a related analysis step may occur. For instance, the frequency with which an item in the item set 200 is used in traditional practice to assess a patient in a medical setting may be analyzed. Alternately, the cost of equipment to conduct the item may be assessed. The clinical literature may be reviewed to identify the outcomes measures with items in the item set 200 that are psychometrically acceptable and clinically useful. For instance, the reliability and validity of an outcomes measure with one or more items in the item set 200 may be reviewed to ensure it is psychometrically acceptable. As another example, each outcomes measure and/or item may be reviewed to ensure it is clinically useful. For example, while there are many items used to test a person's balance that are available in the literature, not all of them are appropriate for patients in a rehabilitation context. Based on these and similar factors, the initial set of items may be narrowed to reduce the burden to patients, clinicians, and other health care providers.

In 104, a revised plurality of items is collected. A pilot study may be conducted on the plurality of items. The pilot study may be conducted by having clinicians assess patients on the revised items in a standardized fashion, such that each clinician assesses each patient using all of the revised items. In another embodiment, the clinicians may select which items should be used to assess a patient, based on the patient's particular clinical characteristics. The determination as to selection of specific items may be made based on information received during the patient's rehabilitation stay, for instance, at the inpatient evaluation at admission. The item may be administered at least twice during the patient's inpatient stay in order to determine patient progress. The pilot study may be facilitated using an electronic medical record system, such that clinicians enter item scores into the electronic medical record.

In 105, a pilot study analysis may be performed. For instance, items that take too much time for a clinician to conduct with a patient may be removed.

In 106, the original paper-based items for the preliminary outcomes measure 100 are implemented in an electronic medical record. Individual item-level rating can be recorded electronically. For instance, the items to be implemented may be the items that are the result of the pilot study analysis in 105. However, pilot study analysis is not required. Alternately, the items in the preliminary outcomes measure 100 could be implemented in an electronic system, such as a database, that is external to an electronic medical record. In one embodiment, the external electronic system may be in communication with the electronic medical record, using methods that are known in the art, such as database connection technologies. In 107, the items for the preliminary outcomes measure 100 are programmed into the EMR using known methods, allowing clinicians to input their ratings into the electronic medical record. In an embodiment, the EMR may provide a prompt to alert, remind, and/or require the clinician to enter certain ratings for certain items of the preliminary outcomes measure 100. Such prompts may improve the reliability and completeness of clinician data entry into the EMR.

Although the discussion above with reference to FIG. 1 refers to the selection of certain items from various outcome measures, it should be understood that a similar method may be conducted with respect to the selection of the outcome measures themselves. For example, in 104, instead of selecting which items to be used in assessing a patient, the entire outcome measure could be selected or disregarded.

Figure 2:
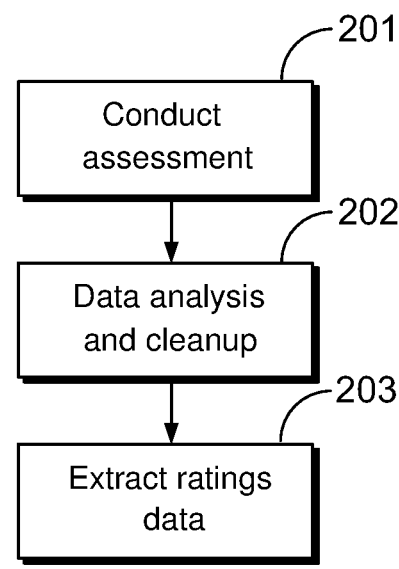

FIG. 2 displays a flowchart for electronically collecting ratings for the items in the preliminary outcomes measure 100. In 201, a clinician conducts an assessment on a patient. In one embodiment, the clinician may conduct the assessment using every item in the preliminary outcomes measure 100. In another embodiment, the clinician may conduct those tests or items in the preliminary outcomes measure 100 that are specific to that clinician's scope of practice. For example, a physical therapist may conduct those tests or item in the preliminary outcomes measure 100 that are specific to physical therapy. In yet another embodiment, the clinician may use her clinical judgement, based on her education, training, and experience, to identify the tests in the preliminary outcomes measure 100 that are most relevant to the patient. If the patient is very ill or has very limited functioning, the clinician will know not to conduct certain items. For instance, a clinician would not ask a newly quadriplegic patient to perform a test that would require the patient to walk.

The assessment may be an initial assessment conducted at or shortly after the time of admission of the patient to a hospital. In an embodiment, each patient receiving care during a period of time, such as a month or a year, is assessed. In another embodiment, a majority of patients receiving care during a period of time are assessed. In yet another embodiment, a plurality of patients are assessed. In other embodiments, the patient population may be refined to include only inpatients, only outpatients, or a combination thereof.

In various embodiments, certain tests in the preliminary outcomes measure 100 may be conducted once at or shortly after admission, and again at or shortly prior to discharge. In various embodiments, certain tests in the preliminary outcomes measure 100 may be conducted weekly. In various embodiments, certain tests in the preliminary outcomes measure 100 may be conducted more than once per week, such as twice per week.

In an embodiment, the assessments may be conducted in a centralized location specific to conducting assessments. The assessments may be conducted by a set of clinicians whose specific function is to conduct assessments. A centralized location with qualified staff and adequate equipment to objectively assess a patient's functional performance may be conducted through a standardized process in a controlled and safe environment. In an embodiment, a clinician provides an order for a lab technician assessment. For example, a clinician (such as a physiatrist, therapist, nurse, or psychologist) orders a specific test (such as a test of gait and balance) or a group of tests. The test order may be sent electronically to the assessment department ("AAL") and a hard copy may be printed for the patient. When the AAL is ready, the patient may travel to the AAL, with assistance if necessary. Staff, such as a technician, performs the ordered test(s). Test results may be recorded and entered/transmitted into the electronic medical record. The clinician may review test results to modify care plan if necessary. This process can reduce the amount of time clinicians require to learn how to conduct a test. One benefit of an AAL is that other clinicians do not need to learn how to conduct various tests every time a new test is introduced. Clinicians will only need to learn how to read the test results, not how to conduct the test. Qualified personnel with proper training can perform the tests. Clinical staff can focus on treatment rather than on assessment. More treatment sessions or additional time can be provided to improve outcomes. Test equipment is centrally kept to reduce the need for multiple units and maintenance costs. Tests can be conducted in a well-controlled, standardized and safe environment. The technician may utilize standardized procedures to avoid potential rater induced bias (tendency for higher ratings to show improvement over time), thus improving data quality.

The ratings from each assessment may be saved in the EMR. For instance, they may be saved in a preliminary ratings dataset 150. In 202, data analysis and cleanup may be performed on the preliminary ratings dataset 150 to improve data quality. For example, out-of-range ratings may be removed from the preliminary ratings dataset 150. Patterns of data in the preliminary ratings dataset 150 from the same clinician may be reviewed and cleaned using methods known in the art. Ratings in the preliminary ratings dataset 150 from patients that show a large increase in rating from "dependent" to "independent" may also be discarded. Suspect data from a particular evaluation may be discarded.

In 203, the ratings data may be further extracted, cleaned, and prepared using methods known in the art to get the data in a form in which the data may be queried and analyzed. Data may be reviewed for quality, and various data options, such as data pivoting, data merging, and creation of a data dictionary may be performed for the preliminary ratings dataset 150. Data from the preliminary ratings dataset 150 may be stored in the EMR or in a different form, such as in a data warehouse, for further analysis. It will be understood by one of ordinary skill in the art that many ways exist to structure the data in the preliminary ratings dataset 150 for analysis. In one embodiment, the preliminary ratings dataset 150 is structured so that item ratings are available for analysis across a plurality of dimensions, such as time period and patient identification.

Once the preliminary ratings dataset 150 has been prepared for analysis, a psychometric evaluation may be performed on the preliminary ratings dataset 150. A psychometric evaluation assesses how well an outcomes measure actually measures what it is intended to measure. A psychometric evaluation may include a combination of classical test theory analysis, factor analysis, and item response theory, and assesses the preliminary ratings dataset 150 for various aspects, which may include reliability, validity, responsiveness, dimensionality, item/test information, differential item functioning, and equating (score crosswalk). In one embodiment, classical test theory analysis may be employed to review the reliability of the items in the preliminary outcomes measure 100, and how the preliminary outcomes measure 100 and the domain work together.

Item Reduction.

The item reduction step 152 assists in reducing the items from the preliminary outcomes measure 100 that do not work as anticipated. Factors can include reliability, validity, and responsiveness (also known as sensitivity to change). The purpose of the item reduction step 152 is to eliminate potential item content redundancy from items in the preliminary outcomes measure 100 to a minimal subset of items in an IRT outcomes measure 180 without sacrificing the psychometric properties of the data set. The item reduction step 152 may be performed using a computer or other computing device, for instance, using a computer program 125. The computer program 125 may be written in the R programming language or another appropriate programming language. The computer program 125 provides an option to allow the number of desired items (as well as options to include specific items) to be specified and computes the Cronbach's coefficient α reliability estimate for every possible combination of items within those user-defined constraints. Acceptable ranges of Cronbach's coefficient α may also be defined in the computer program 125. Additionally, the computer program 125 may construct and run syntax for a statistical modeling program, such as Mplus (Muthen & Muthen, Los Angeles, Calif., http://www.statmodel.com) to determine the fit of a 1-factor confirmatory factor analysis (CFA) model to each reduced subset 155 of items.

The computer program 125 may be used to analyze several of the outcomes measures included in the preliminary outcomes measure 100 (such as the FIST, BBS, FGA, ARAT, and MASA), and searched for unidimensional subsets between four and eight items with Cronbach's α reliabilities between 0.70 and 0.95. Using these constraints, the number of items in many measures may be reduced substantially. For instance, measures may be reduced by at least half of their original length while maintaining good psychometric properties. The resulting item subsets served as building blocks for the confirmatory factor analysis (CFA). In an embodiment, certain items may not be included in the item reduction process, such as the items from the FIM®. In an embodiment, the item reduction step 152 may performed multiple times. For instance, it may be performed on each outcomes measure included in the preliminary outcomes measure 100.

In the item reduction step 152, the computer program 125 determines the extent to which items are related to each other. The computer program 125 may determine the extent to which items within an outcomes measure in the preliminary outcomes measure 100 are related to each other. In one embodiment, items are related to each other within an outcomes measure if they have responses which correlate highly. The analysis may start by providing an initial core set of items, the number of which may be determined with clinician input, based on correlations between item pairs. For example, the computer program 125 may determine how item A relates to item B, where item A and item B are both in the same outcomes measure. If there is a high correlation, both item A and item B are included in the core set. Then, the computer program 125 may determine how new item C correlates to the set of items {A, B}. If there is a high correlation, item C is included in the core set. The method may be repeated with additional items, D, E, F, etc. As described above, the program assess the reliability (Cronbach's α) of every possible subset of items. The program correlates the responses from one set of items with the responses from a second set of items. Chronbach's α is known in the art but a brief example is hereby provided. The information used in computing Cronbach's α are the correlations between every possible split-half in the subset of items. For example, using 3 items {A, B, C}, Cronbach's α averages the correlations A vs. BC, B vs. AC, and C vs. AB. In other words, the correlations are computed between every pair of unique subsets of a set. The purpose of the correlational analysis is to help ensure that items are measuring the same underlying construct and improving reliability.

Table 1 lists an exemplary output of the item reduction step 152 for the Berg Balance Scale ("BBS") outcomes measure, setting the sample size equal to five items. The numbers in each cell in the "item" columns reflect the number of the question on the BBS (1: sitting unsupported; 2: change of position—sitting to standing; 3: change of position—standing to sitting; 4: transfers; 5: standing unsupported; 6: standing with eyes closed; 7: standing with feet together; 8: tandem standing; 9: standing on one leg; 10: turning trunk (feet fixed)). Each reduced subset 155 is shown along with its associated Cronbach's α value. The first reduced subset has the highest Cronbach's α of the reduced subsets in Table 1. In one embodiment, the reduced subset with the highest Cronbach's α is used as the initial reduced subset for the CFA step 160, which is described below in further detail.

TABLE 1

| Grouping | Item 1 | Item 2 | Item 3 | Item 4 | Item 5 | Cronbach's α |
| --- | --- | --- | --- | --- | --- | --- |
| 1 | 1 | 2 | 4 | 5 | 6 | 0.9594018 |
| 2 | 1 | 2 | 4 | 6 | 7 | 0.9592235 |
| 3 | 1 | 2 | 4 | 6 | 8 | 0.9584257 |
| 4 | 1 | 2 | 4 | 6 | 10 | 0.9583003 |
| 5 | 2 | 6 | 7 | 8 | 10 | 0.9552663 |
| 6 | 1 | 2 | 4 | 6 | 9 | 0.9550176 |
| 7 | 2 | 4 | 6 | 8 | 10 | 0.9549165 |
| 8 | 2 | 4 | 6 | 7 | 10 | 0.9547042 |
| 9 | 2 | 4 | 6 | 7 | 8 | 0.9539102 |
| 10 | 1 | 2 | 6 | 8 | 10 | 0.9538519 |

Confirmatory Factor Analysis.

Factor analysis is a statistical method that is used to determine the number of underlying dimensions contained in a set of observed variables and to identify the subset of variables that corresponds to each of the underlying dimensions. The underlying dimensions can be referred to as continuous latent variables or factors. The observed variables (also known as items) are referred to as indicators. Confirmatory factor analysis (CFA) can be used in situations where the dimensionality of a set of variables for a given population is already known because of previous research. CFA may be used to investigate whether the established dimensionality and factor-loading pattern fits a new sample from the same population. This is the "confirmatory" aspect of the analysis. CFA may also be used to investigate whether the established dimensionality and factor-loading pattern fits a sample from a new population. In addition, the factor model can be used to study the characteristics of individuals by examining factor variances and covariances/correlations. Factor variances show the degree of heterogeneity of a factor. Factor correlations show the strength of association between factors.

Confirmatory factor analysis (CFA) may be performed using Mplus or other statistical software to validate how well the item composition within the pre-specified factor structure holds statistically. CFA is characterized by restrictions on factor loadings, factor variances, and factor covariances/correlations. CFA requires at least m^2 restrictions where m is the number of factors. CFA can include correlated residuals that can be useful for representing the influence of minor factors on the variables. A set of background variables can be included as part of a CFA.

Mplus can estimate CFA models and CFA models with background variables for a single or multiple groups. Factor indicators for CFA models can be continuous, censored, binary, ordered categorical (ordinal), counts, or combinations of these variable types. When factor indicators are all continuous, Mplus has seven estimator choices: maximum likelihood (ML), maximum likelihood with robust standard errors and chi-square (MLR, MLF, MLM, MLMV), generalized least squares (GLS), and weighted least squares (WLS) also referred to as ADF. When at least one factor indicator is binary or ordered categorical, Mplus has seven estimator choices: weighted least squares (WLS), robust weighted least squares (WLSM, WLSMV), maximum likelihood (ML), maximum likelihood with robust standard errors and chi-square (MLR, MLF), and unweighted least squares (ULS). When at least one factor indicator is censored, unordered categorical, or a count, Mplus has six estimator choices: weighted least squares (WLS), robust weighted least squares (WLSM, WLSMV), maximum likelihood (ML), and maximum likelihood with robust standard errors and chi-square (MLR, MLF).

Using the highly-reliable subsets of items from the measure reduction step, a model may be defined in statistical software such as Mplus that hypothesizes that all items within a domain are interrelated. The model also may measure specific constructs under the preview of that domain. For example, all item subsets taken from Self Care measures may be hypothesized to measure Self Care, but also simultaneously measure one of Balance, Upper Extremity Function, and Swallowing. Constructing the model in this way allows for the measurement of both an overall domain (e.g., Self Care) as well as a set of interrelated constructs that compose that domain (e.g., Balance, UE Function, and Swallowing—the constructs composing Self Care). Given the data, the structure of the model implies a set of expected correlations between each pair of items. However, these (polychoric) correlations can be computed directly from the data. These are the observed correlations. The appropriateness of the constructed model, called "model fit" in statistics, may be determined using the root mean square error of approximation (RMSEA), which is a measure of the difference between the observed and expected correlations. In a preferred embodiment, if the value of that difference is low (for instance, less than 0.08) the model has acceptable fit.

After applying the CFA step 160 on a reduced subset 155, the output of the CFA step 160 may contain factor loadings, including a General Factor loading. The General Factor loading may be between −1 and 1, with values of the General Factor loading of between 0.2-0.7 indicating whether a factor assesses the relevant item well. The output of the CFA step 160 may provide additional factor loadings for each item. In an embodiment, each item may have a factor loading for each sub-domain. For instance, each item may have a factor loading value for Balance, a factor loading value for Upper Extremity, a factor loading value for Swallowing, and a factor loading value for each other sub-domain. Where the item is relevant to a sub-domain, the factor loading value will be non-zero, in an embodiment.

In certain instances, applying the CFA step 160 on a reduced subset 155 can create problems that require selection of a new reduced subset 155. For instance, a general factor loading value higher than 0.7, or particularly a value closer to 1.0, indicates redundancy. For instance, the way items are scored on the Action Research Arms Test (ARAT) outcomes measure necessarily forces too high of a reliability. Patients who achieve a maximum score on the first (most difficult) item are credited with having scored 3 on all subsequent items on that scale. If the patient scores less than 3 on the first item, then the second item is assessed. This is the easiest item, and if patients score 0 then they are unlikely to achieve a score above 0 for the remainder of the items and are credited with a zero for the other items. This method of scoring forces the too-high reliability. In other instances, if a factor loading value is greater than 1, it reflects that a pair of items has a negative variance (which is not possible) and so the CFA step 160 must be run on a new reduced subset 155. A new reduced subset 155 may be selected from the group of reduced subsets generated by item reduction step 152. For instance, new reduced subset may be selected that has the next-highest Chronbach's α, then applying CFA step 160 to the new reduced subset.

Additionally, during the process of running the CFA step 160, it may be apparent that items designated by clinicians as falling within one sub-domain should be moved to a different sub-domain in order to improve the fit of the model used to generate the IRT outcomes measure 180 (discussed further below). For example, during the development of the embodiments described herein, items identified by clinicians as relating to "Strength" were initially placed in the Self-Care domain. In running the CFA step 160, however, it was determined that these items did not fit the model. Moving these items to the "Upper Extremity Function" sub-domain improved the fit of the model.

Table 2 below shows the fit statistics of a 1-factor CFA containing groupings 1-10 set out in Table 1. In the CFA step 160, an assessment may be conducted as to whether the fit statistics listed in Table B meet usual "good fit" criteria. In one embodiment, these criteria are RMSEA<0.08, CFI>0.95, TLI>0.95, and WRMR<1.00. Those of ordinary skill in the art will appreciate that other good fit criteria could be used.

TABLE 2

| Grouping | fac | rmsea | cfi | tli | wrmr | Meets Criteria? |
|---|---|---|---|---|---|---|
| 1 | 1 | 0.145 | 0.999 | 0.997 | 0.016 | No |
| 2 | 1 | 0.155 | 0.998 | 0.997 | 0.017 | No |

TABLE 2-continued

| Grouping | fac | rmsea | cfi | tli | wrmr | Meets Criteria? |
|---|---|---|---|---|---|---|
| 3 | 1 | 0.143 | 0.999 | 0.997 | 0.015 | No |
| 4 | 1 | 0.148 | 0.998 | 0.997 | 0.017 | No |
| 5 | 1 | 0.09 | 0.999 | 0.999 | 0.009 | No |
| 6 | 1 | 0.126 | 0.999 | 0.998 | 0.014 | No |
| 7 | 1 | 0.076 | 1 | 0.999 | 0.008 | Yes |
| 8 | 1 | 0 | 1 | 1 | 0.002 | Yes |
| 9 | 1 | 0.028 | 1 | 1 | 0.004 | Yes |
| 10 | 1 | 0.09 | 0.999 | 0.999 | 0.009 | No |

Although the example above is given only with respect to one outcomes measure, the Berg Balance Scale, it should be understood that the CFA step 160 is applied to each outcomes measure in the preliminary outcomes measure 100.

Item Response Theory. In an embodiment, the IRT outcomes measure 180 may be structured to contain a plurality of high-level domains. For example, the IRT outcomes measure 180 may be structured to include a "Self Care" domain (which includes items determined to reflect a patient's capability to perform self care), a "Mobility" domain (which includes items determined to reflect a patient's capability to be mobile), and a "Cognition" domain (which includes items determined to reflect a patient's cognitive capabilities). Within each higher-level domain, specific assessment areas, also referred to as "factors" or "clusters," may be identified. Table 3 reflects exemplary assessment areas associated with each higher-level domain.

TABLE 3

| Domain | Areas/Clusters |
|---|---|
| Self-Care | Balance |
| | UE Function |
| | Strength |
| | Changing Body Position |
| | Swallowing |
| Mobility | Balance |
| | W/C Skills |
| | Changing Body Positions |
| | Bed Mobility |
| | Mobility |
| Cognition | Awareness |
| | Agitation |
| | Memory |
| | Speech |
| | Communication |

Because the measurement goals of the IRT outcomes measure 180 involved measuring general domains (i.e., Self Care, Mobility, and Cognition) as well as specific assessment areas within those domains, a bifactor structure for each of the domains may be targeted (the general factor and domain-specific factor). The composition of the specific factors may be determined by the content of each item set. For example, items from the FIST, BBS, and FGA may be combined to form the "Balance" assessment area within the Self Care domain. Acceptable fit of the bifactor model to the data was assessed using the criterion of RMSEA<0.08 (Browne & Cudeck, 1992), and modification indices were also computed to check for local item dependence and potential improvements to the model, such as additional cross-loadings (in other words, an item contributes to several factors).

Item Response Theory reflects a mathematical model that describes the relationship between a person's ability and item characteristics (such as the difficulty). For example, a more able person is more likely to be able to perform a harder task, and can allow a more tailored intervention based on a series of questions. Other item characteristics may be relevant as well, such as an item's "discrimination," which is its ability to distinguish between people with high or low levels of a trait.

After constructing the CFA models for each of the domains, the final structures may be coded to run in an item response theory software package, such as flexMIRT (Vector Psychometric Group, Chapel Hill, N.C., US). flexMIRT is a multilevel, multidimensional, and multiple group item response theory (IRT) software package for item analysis and test scoring. The multidimensional graded response model (M-GRM) may be chosen to account for the ordered, categorical nature of the item responses from the clinician-rated performance ratings. For example, the dimensions may be "Self-Care," "Mobility," and "Cognition". Sub-domains for "Self-Care" may be "Balance, "Upper Extremity Function," "Strength," "Changing Body Position", and "Swallowing." Sub-domains for "Mobility" may be Balance, Wheelchair ("W/C") Skills, Changing Body Positions, Bed Mobility, and Mobility. Sub-domains for "Cognition" may be "Awareness," "Agitation," "Memory," "Speech," and "Communication."

In a preferred embodiment, however, sub-domains may be reduced in order to focus on key subdomains of ability. For "Self-Care", for example, these may be Balance, UE Function, and Swallowing. For "Cognition" these may be Cognition, Memory, and Communication. For "Mobility," there may be no sub-domains—in other words, the sub-domains may all be clustered together.

The analysis also may be multigroup in nature. For example, the Self Care and Mobility samples may be split into groups determined by the level of balance (sitting, standing, or walking). As another example, the Cognition sample may be split into broad diagnostic categories (stroke, brain injury, neurological, or not relevant). In an embodiment, in order to accommodate the complexity of the models, the Metropolis-Hastings Robbins-Monro (MH-RM) algorithm (Cai, 2010) may be used for more efficient parameter estimation. MH-RM cycles through the following three steps repeatedly until the differences between two consecutive cycles are smaller than a chosen criterion. In Step 1 (Imputation), random samples of the latent traits are imputed from a distribution implied by the item parameter estimates taken from the preceding cycle. If it is the first cycle, then the distribution implied by the algorithm's starting values are used. This imputation can be performed using the MH sampler. In Step 2 (Approximation), the log-likelihood of the imputed data is evaluated. In Step 3 (Robbins-Monro Update), new parameter estimates for the next cycle are computed by using the Robbins-Monro filter on the log-likelihood in step 2. Step 1 is then repeated using the information from Step 3. Slopes can reflect item discriminations and intercepts can reflect item difficulties.

In addition to the item slopes and intercepts, maximum a posteriori (MAP) latent trait scores, which reflect the patient's level of ability, may be computed for each patient.

The principal coding for IRT focuses on translating the mathematical structure chosen after CFA into one that can be assessed using IRT. The data used for the analysis may be, for instance, simply the patients' ratings on all items on which they were assessed. For consistency, the most recent available data for each patient on each item they were administered may be used. This has the convenience of putting patient scores in a particular frame of reference: typical discharge level. MAP (maximum a posteriori) scoring may be used, but other scoring methods are known which could be employed instead, such as ML (maximum likelihood), EAP (expected a posteriori), or MI (multiple imputation). Additionally there are different estimation methods that could be employed. For instance, marginal maximum likelihood using the expectation-maximization algorithm (MML-EM) may be used. However, this method can suffer when working with more than a few dimensions. In a preferred embodiment, the Metropolis-Hastings Robbins-Munro (MH-RM) estimation is used.

Maximum a posteriori (MAP) scoring requires two inputs: the scoring density of the population (usually assumed to be standard normal for each dimension) and the IRT parameters for each item that a patient was rated on. Multiplying the population density by the IRT functions for each item results in what is known as a likelihood—in other words, mathematical representation of the probability of various scores, given what is known about the items and how the patient was rated on each of the items. The location of the maximum value of that function is the patient's MAP score.

Sometimes, response options on an item are only selected very rarely, which may cause problems with estimating IRT parameters for that item (and also implies that that response option may have been unnecessary). In such cases, those responses can be collapsed into an adjacent category. For example, if an item has responses {1, 2, 3, 4} and response 2 is very rarely seen in the data, we may recode the data {1, 2, 2, 3}. It should be understood that the actual value of the number is unimportant in IRT analysis, and that instead, the ordinality matters.

Group composition: The IRT analyses used here can be multigroup in nature to allow for more targeted assessment. For Self Care and Mobility, patients may be grouped according to their level of balance (none, sitting, standing, and walking). Similarly, groups may be formed in the cognitive domain according to their cognitive diagnosis (stroke, brain injury, neurological, or none). This method can result in multiple test forms that only contain items appropriate for each patient. For instance, they may contain test forms as follows: for "Self-Care" and "Mobility", no balance, sitting balance, (up to) standing balance, and no balance restrictions; for "Cognition," stroke, brain injury, neurological, or not disordered. The forms may tailored according to group membership, rather than to assessment areas. For example, the patient's balance level may affect which balance measure items appear on the Self Care and Mobility domains, while the patient's cognitive diagnosis (if any) may affect which measures may appear on the form. For instance, the ABS is only used on the Brain Injury form of the Cognition measure and the KFNAP is only used on the Stroke measure.)

Item response theory results in a distinct score for each domain. For example, a patient may score a 1.2 in the "Self-Care" domain, a 1.4 in the "Mobility" domain, and a 3 in the "Cognition" domain. In an embodiment, these scores may be reported to clinicians, patients, and others separately. In other embodiments, these scores may be combined into a single score. In an embodiment, a score of +1 means the patient is 1 logit above average. A score of −1 means the patient is 1 logit below average. Values below −3 and above 3 are highly improbable, because the mathematical assumptions underlying IRT are such that scores follow an average distribution. It should be recognized by one or ordinary skill in the art that other numbers reflecting the standard deviation and logit could be employed instead. For instance, a score of 3 could mean the patient is average, so scores would range between 0 and 6. As another example, a score of 50 could mean the patient is average, and a score of +10 could mean that the patient is 1 logit above average, so scores would range from 20 to 80.

An example of running the IRT step 170 is now provided, with respect to the Self-Care domain. Seven factors are provided to the IRT step 170: the Self Care factor, the Balance factor, the UE Functioning factor, the Swallowing factor, a hidden factor for ARAT, a hidden factor for overcoming a negative correlation between the FIST and FGA outcomes measures, and a hidden factor specific to the FIST so it is not overweighted in the result. The IRT step 170 (for instance, using the MH-RM estimation) returns a discrimination matrix 172 and a difficulty matrix 174. For instance, these matrices may be presented in slope/intercept formulation, where slope reflects item discrimination and intercept reflects item difficulty.

Table 4 displays an exemplary discrimination matrix 172 for the Self-Care domain of an exemplary IRT outcomes measure 180. The column headings a1-a7 in Table 4 represent the following, with "hidden" factors listed in parentheses: (a1: Self Care; a2: (ARAT local dependence); a3: Upper Extremity Function; a4: Swallowing; a5: Balance; a6: (Reduction of FIST influence); a7: (Negative relationship of BBS and FGA)). Table 4 lists the slope values for each item for each factor a1-a7. The item naming in Table 4 is also reflected in Table 6 in Appendix 1, listing the items in an exemplary IRT outcomes measure 180.

TABLE 4

| | Item | a1 | (a2) | a3 | a4 | a5 | (a6) | (a7) |
|---|---|---|---|---|---|---|---|---|
| 6 | anteriorNudge | 2.36 | 0 | 0 | 0 | 2.71 | 5.86 | 0 |
| 7 | staticSitting | 2.35 | 0 | 0 | 0 | 2.8 | 6.07 | 0 |
| 8 | sittingEyesClosed | 2.15 | 0 | 0 | 0 | 2.55 | 5.37 | 0 |
| 9 | sittingLiftFoot | 1.99 | 0 | 0 | 0 | 2.23 | 4.86 | 0 |
| 10 | lateralReach | 2.25 | 0 | 0 | 0 | 2.5 | 5.45 | 0 |
| 11 | pickUpFromFloor | 1.78 | 0 | 0 | 0 | 1.92 | 4.3 | 0 |
| 1 | standingToSitting | 0.7 | 0 | 0 | 0 | 4.05 | 0 | 2.44 |
| 2 | stUnFtTgthr | 0.89 | 0 | 0 | 0 | 5.65 | 0 | 3.4 |
| 3 | rFwdArm | 0.75 | 0 | 0 | 0 | 4.38 | 0 | 2.93 |
| 4 | pickObjSt | 0.72 | 0 | 0 | 0 | 4.24 | 0 | 2.79 |
| 5 | turn360 | 0.92 | 0 | 0 | 0 | 5.25 | 0 | 3.48 |
| 12 | levelSurface | 1.01 | 0 | 0 | 0 | 1.81 | 0 | −2.08 |
| 13 | verticalHeadTurns | 0.95 | 0 | 0 | 0 | 1.86 | 0 | −1.93 |
| 14 | pivotTurn | 1.17 | 0 | 0 | 0 | 2.15 | 0 | −2.33 |
| 15 | stepOverObstacle | 1.03 | 0 | 0 | 0 | 2.04 | 0 | −2.19 |
| 16 | ambulatingBackwards | 1.05 | 0 | 0 | 0 | 2.02 | 0 | −2.17 |
| 17 | graspWood2p5 | 0.77 | 4.62 | 4.57 | 0 | 0 | 0 | 0 |
| 18 | gripPourWater | 0.87 | 5.11 | 5.61 | 0 | 0 | 0 | 0 |

TABLE 4-continued

| | Item | a1 | (a2) | a3 | a4 | a5 | (a6) | (a7) |
|---|---|---|---|---|---|---|---|---|
| 19 | pinchBearing3rd | 0.67 | 3.38 | 4.6 | 0 | 0 | 0 | 0 |
| 20 | grossHandToMouth | 0.48 | 3.24 | 3.21 | 0 | 0 | 0 | 0 |
| | nhpLpoly | 0 | 0 | 2.32 | 0 | 0 | 0 | 0 |
| | nhpRpoly | 0 | 0 | 2.21 | 0 | 0 | 0 | 0 |
| | bbLpoly | 0 | 0 | 3.63 | 0 | 0 | 0 | 0 |
| | bbRpoly | 0 | 0 | 3.4 | 0 | 0 | 0 | 0 |
| 24 | salivaC | 1.84 | 0 | 0 | 2.99 | 0 | 0 | 0 |
| 25 | tongueMovementC | 3.42 | 0 | 0 | 5.97 | 0 | 0 | 0 |
| 26 | tongueStrengthC | 3.26 | 0 | 0 | 5.6 | 0 | 0 | 0 |
| 27 | tongueCoordinationC | 2.79 | 0 | 0 | 4.8 | 0 | 0 | 0 |
| 28 | oralPreparationC | 2.31 | 0 | 0 | 4.04 | 0 | 0 | 0 |
| 29 | bolusClearanceC | 2.57 | 0 | 0 | 4.27 | 0 | 0 | 0 |
| 30 | oralTransitC | 2.46 | 0 | 0 | 4.22 | 0 | 0 | 0 |
| 31 | voluntaryCoughC | 1.59 | 0 | 0 | 2.74 | 0 | 0 | 0 |
| 32 | pharyngealPhaseC | 2.11 | 0 | 0 | 3.67 | 0 | 0 | 0 |
| 33 | pharyngealResponseC | 1.29 | 0 | 0 | 2.2 | 0 | 0 | 0 |
| | foisC | 1 | 0 | 0 | 1.62 | 0 | 0 | 0 |
| | ricdssC | 1.32 | 0 | 0 | 1.88 | 0 | 0 | 0 |
| | eatingC | 2.37 | 0 | 0 | 0 | 0 | 0 | 0 |
| | groomingC | 3.49 | 0 | 0 | 0 | 0 | 0 | 0 |
| | bathingC | 3.9 | 0 | 0 | 0 | 0 | 0 | 0 |
| | dressingUpperC | 4.87 | 0 | 0 | 0 | 0 | 0 | 0 |
| | dressingLowerC | 5.63 | 0 | 0 | 0 | 0 | 0 | 0 |
| | toiletingC | 5.08 | 0 | 0 | 0 | 0 | 0 | 0 |

Table 5 displays an exemplary difficulty matrix 174 for an IRT outcomes measure 180. Table 5 displays the intercept values for each item, for each factor d1-d6. The column headings d1-d6 in Table 5 represent the following, with "hidden" factors listed in parentheses: (d1: Self Care; d2: (ARAT local dependence); d3: Upper Extremity Function; d4: Swallowing; d5: Balance; d6: (Reduction of FIST influence)).

TABLE 5

| Item | d1 | (d2) | d3 | d4 | d5 | (d6) |
|---|---|---|---|---|---|---|
| anteriorNudge | 9.88 | 8.52 | 6.16 | 5.29 | | |
| staticSitting | 13.1 | 9.96 | 7.88 | 6.48 | | |
| sittingEyesClosed | 9.4 | 7.99 | 6.39 | 5.08 | | |
| sittingLiftFoot | 7.12 | 5.88 | 4.37 | 3.28 | | |
| lateralReach | 7.92 | 5.35 | 3.48 | 2.15 | | |
| pickUpFromFloor | 4.82 | 3.74 | 2.69 | 1.71 | | |
| standingToSitting | 2.07 | 0.65 | −0.24 | −3.13 | | |
| stUnFtTgthr | 0.04 | −1.88 | −2.36 | −6 | | |
| rFwdArm | 0.19 | −2.63 | −3.3 | −5.7 | | |
| pickObjSt | −1.36 | −1.87 | −2.01 | −5.63 | | |
| turn360 | −2 | −4.96 | −7.25 | −7.79 | | |
| levelSurface | 4.18 | 0.41 | −2.28 | | | |
| verticalHeadTurns | 3.64 | 1.1 | −2.5 | | | |
| pivotTurn | 3.92 | 0.83 | −1.89 | | | |
| stepOverObstacle | 3.22 | −0.87 | −2.93 | | | |
| ambulatingBackwards | 3.07 | 0.29 | −3.45 | | | |
| graspWood2p5 | 5.25 | 3.4 | −0.19 | | | |
| gripPourWater | 4.22 | 2.54 | −2.2 | | | |
| pinchBearing3rd | 0.66 | −2.66 | | | | |
| grossHandToMouth | 5.68 | 4.1 | 1.24 | | | |
| nhpLpoly | 1.57 | 0.14 | −1.17 | | | |
| nhpRpoly | 1.75 | 0.44 | −0.81 | | | |
| bbLpoly | 1.74 | 0.08 | −1.92 | | | |
| bbRpoly | 1.95 | 0.1 | −1.72 | | | |
| salivaC | 3.78 | 2.76 | 1.01 | 0.35 | | |
| tongueMovementC | 5.26 | 2.22 | −0.26 | −3.66 | | |
| tongueStrengthC | 0.39 | −1.37 | −4.94 | | | |
| tongueCoordinationC | 3.11 | −0.08 | −3.2 | | | |
| oralPreparationC | 1.23 | 0.76 | 0.11 | −2.09 | | |
| bolusClearanceC | 1.42 | −0.5 | −4.08 | | | |
| oralTransitC | 2.95 | 1.53 | −0.44 | −3.33 | | |
| voluntaryCoughC | 1.15 | −0.11 | −1.56 | | | |
| pharyngealPhaseC | 3.66 | 1.45 | −3.12 | | | |
| pharyngealResponceC | 2.3 | −0.14 | | | | |
| foisC | 0.8 | 0.41 | 0.18 | −0.02 | −0.79 | −1.05 |
| ricdssC | 1.68 | 0.58 | −0.29 | −1 | −1.65 | |

TABLE 5-continued

| Item | d1 | (d2) | d3 | d4 | d5 | (d6) |
|---|---|---|---|---|---|---|
| eatingC | 2.37 | 1.9 | 1.55 | −1.32 | −3.26 | |
| groomingC | 3.31 | 1.77 | 0.74 | −3.09 | −8.07 | |
| bathingC | 1.72 | 0.63 | −0.74 | −2.35 | −6.73 | |
| dressingUpperC | 3.62 | 2.24 | 0.94 | −0.62 | −4.97 | −11.37 |
| dressingLowerC | 1.67 | −0.15 | −1.58 | −3.7 | −7.37 | −14.8 |
| toiletingC | 0.72 | −0.48 | −1.47 | −2.92 | −6.25 | |

It should be understood that discrimination matrix 172 and a difficulty matrix 174 may be prepare for each domain in the IRT outcomes measure 180.

An exemplary score/probability response may be plotted, where the X-axis reflects the score and the Y-axis reflects the probability of response. The product of the curves results in a likelihood curve that somewhat appears like a bell curve. The peak of the curve can be used as the score for the patient.

Input from Therapists to Ensure Clinical Relevance.

Each item may be labeled with a cluster that most appropriately describes its role in the IRT outcomes measure 180. This labeling may be done by clinicians on the basis of their education, training, and experience. For example, a clinician may label an item that measures balance, such as items that test function in sitting, as falling within the "Mobility" domain and the "Balance" factor in Table 1.

Because item selection (retention or removal) in the item reduction step of the analysis is predicated on psychometric and statistical evaluations, in an embodiment, clinical experts may review the item content covered in the reduced item sets for further feedback. For example, a pool of clinicians may be surveyed for input on whether items should be added or removed from the subsets taken from each of the full outcomes measures. Their input may be used to construct the final models for each domain, to help ensure the retained items are psychometrically sound and clinically relevant.

Remodeling to Derive Final Sets of Items.

After the negotiated item sets, considering both psychometric evaluation and clinical judgement, were in place, the CFA and IRT steps may be carried out. Left-out items with a large clinical endorsement may be added back into the models, while included items with low endorsement may be removed. The fit of the models to the data may then be assessed using the root mean square error of approximation (RMSEA) computed during the CFA, and new item parameter estimates and latent trait scores were computed during the IRT analysis. Table 6 in Appendix 1 to this Specification lists the items in a preferred exemplary IRT outcomes measure 180.

Display

Various aspects of data relating to an individual patient's score may be displayed for a clinician and/or a patient.

Figure 3:
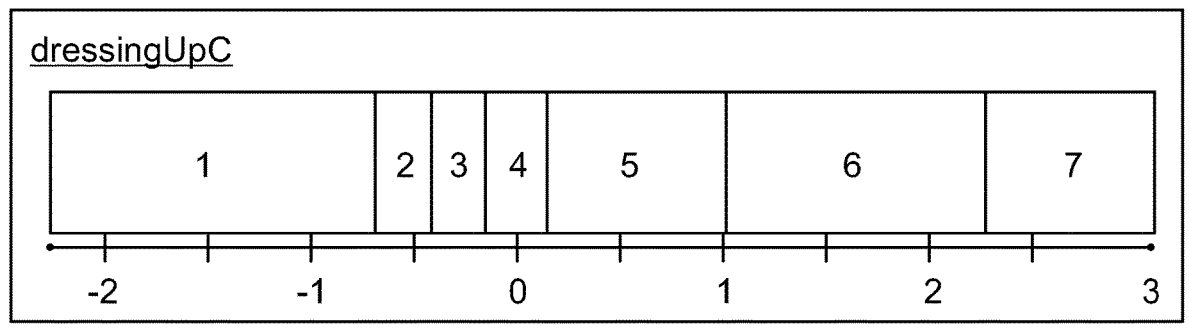

FIG. 3 displays an exemplary scoring system of the IRT, comparing it against a FIM® score known in the prior art. The IRT score reflects the amount of ability that a person, such as a patient, has. The IRT score can be a continuously scaled score across all functional categories. A score of exactly 0 means that the person has average ability at dischare. A score above 0 means that the person has above average ability. A score below 0 means that the person has below average ability. FIG. 3 displays the FIM scoring for a dressing item on the FIM and the continuum of attainable Self Care IRT scores. The FIM scores are reflected by the length of each patterned section. For example, the patterned section labeled "1" reflects a FIM score of 1; the section labeled "2" reflects a FIM score of 2; and so on. Scores and difficulties are presented on the same metric, meaning that if someone has an IRT score of 1.50, they would be expected to score in the 6th category of the item.

The value of the IRT score becomes apparent from an analysis of FIG. 3. Suppose a patient is admitted to an inpatient rehabilitation facility, and their IRT score improves from −1.00 to 0.00. The equivalent change in the FIM level would be a +3. As a result, this would be seen as a good outcome for the patient, as the patient showed functional gains.

However, the FIM score is deficient in showing gains when progress is made within a FIM level. Suppose another patient is admitted with a score of −2.00, and progresses all the way to −1.00. Even though the patient made just as much progress as the previous patient (+1.00), it still looks like the patient has not improved her functional level on upper body dressing, as the change in the FIM for this item is 0. As a result, one benefit of the IRT score is that it can detect improvement where the FIM cannot. In our experience, the expected change in Self Care for individuals with Nontraumatic spinal cord injury and Neurological injuries is fairly dramatic when using the IRT.

Figure 4:
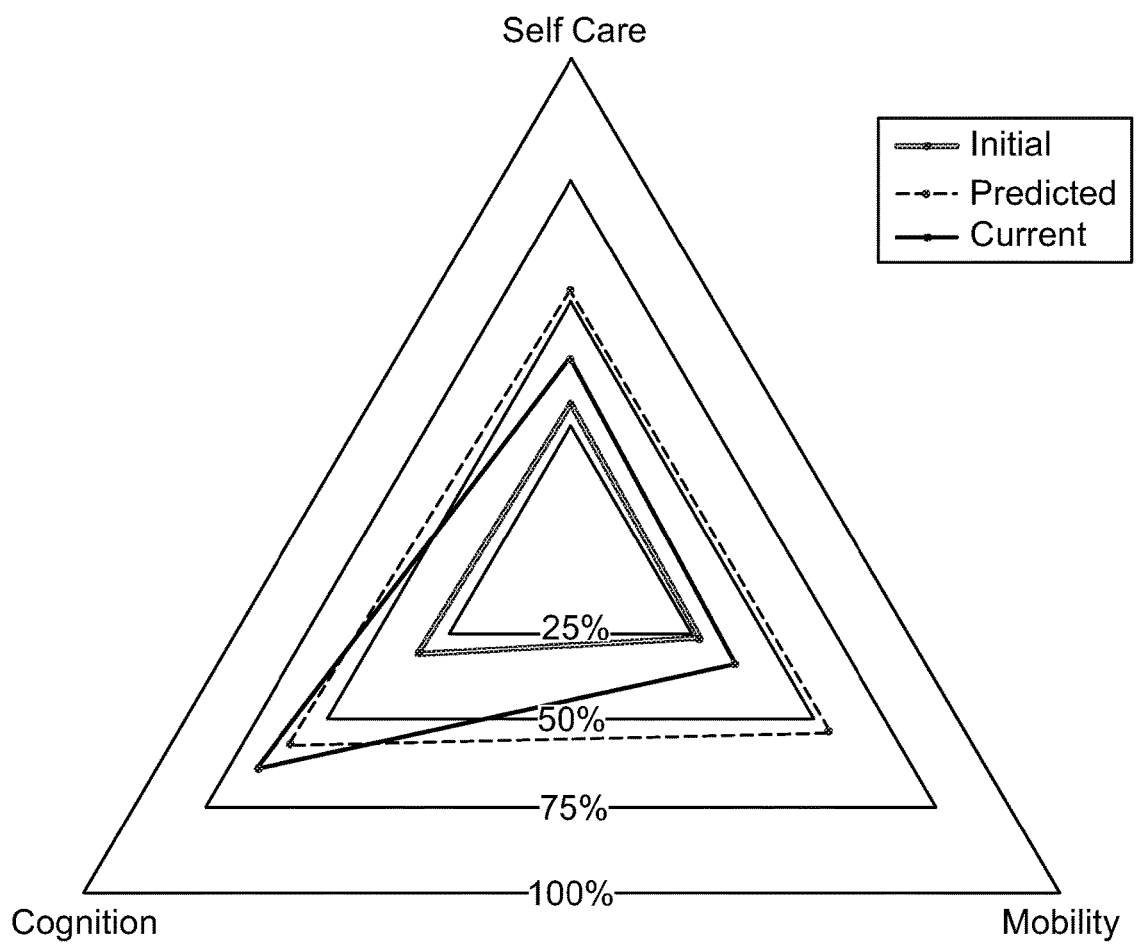

FIG. 4 displays an exemplary plot of certain data relating to patient scores in the Self Care, Cognition, and Mobility domains. The percentage values 25%, 50%, 75%, and 100% reflect the percent of a score on each domain. For instance a score of 100% on the Self Care domain reflects a patient who received the highest possible score on that domain. The solid line triangle reflects the patient's initial scores, which may be tabulated based on assessments at or shortly after admission. The black triangle reflects the patient's current scores. The dashed-lines triangle reflects the patient's predicted scores. By reviewing the scores in this way, a clinician is able to easily determine the domains in which a patient has made improvement and also easily determine the domains where additional therapy or other care may be useful. For instance, after reviewing the plot at FIG. 4, a clinician may determine that further care should be focused in the area of Self Care and Mobility, since those scores are below the predicted scores for those domains.

Prediction estimates may be derived in a variety of ways. In one embodiment, Hierarchical Linear Modeling (HLM) may be used, incorporating information regarding past patients' diagnoses, the severity of those diagnoses (the "case mix group", a measure of the patient's condition's severity within a diagnosis), the days on which measures were administered to the patients, and the scores on those days. The modeling may output a predictive curve for every severity within every diagnosis for up to 50 days of inpatient stay. When plotting the information, the x-axis may be the number of days since admission and the y-axis may be the IRT (MAP) score.

Other methods of prediction could be used, including data science methods like neural networks and random forest models. Furthermore, additional patient information may be incorporated in the prediction process.

In an embodiment, a patient may be assessed using the IRT outcomes measure 180 over multiple days. For instance, the patient may be assessed on a first subset of questions from the IRT outcomes measure 180 on a first day, and then assessed on a second subset of questions on a second day. The data feed may be set up such that it collects the most recent item value.

Adaptive testing may be employed, such that the items in the IRT outcomes measure 180 are selected for assessment in response to the score from an already assessed item. For example, the clinician may assess the patient with the items in the IRT outcomes measure 180 from the FIST test; compute an initial IRT score based off the results; and then select a next item (or a plurality of next items) most appropriate, based on the initial IRT score. This process may be applied iteratively until the patient's score can be determined to be accurate within a pre-determined uncertainty level. For instance, once uncertainty is at or below 0.3, the adaptive testing method may stop providing additional items for assessment and provide a final IRT score for the patient, clinician, or others to review.

Figure 5:
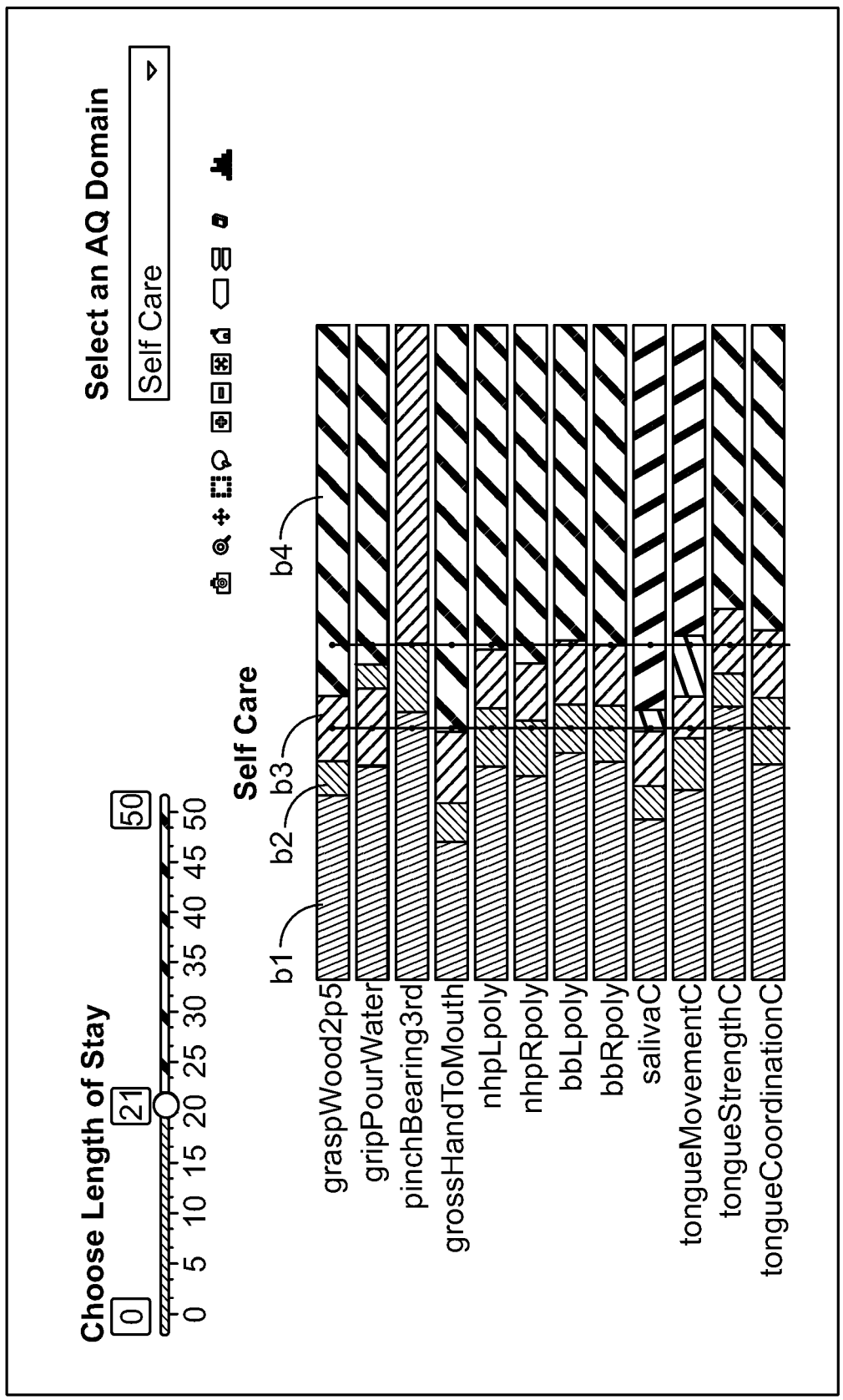

FIG. 5 displays an exemplary chart of certain data relating to patient scores in the Self Care domain. Each row of the chart relates to a single item. For example, the top row relates to the test of grasping a wood block. Each row of the chart is divided into different shadings, as is discussed with respect to FIG. 3. The length of each section reflects how a score on that item relates to the AQ score. For example, section b1 reflects how a score of 1 on a grasping item relates to the AQ score.

FIG. 5 further shows a patient's current and expected functional status on each of the items/tasks in the Self Care domain. It should be understood that this chart could display data from Mobility, Cognition, or other domains. The "Choose Length of Stay" scroll-bar allows a clinician to compare each level of ability on every item (e.g., current vs. expected) for various lengths of stay. This can allow a clinician to determine whether additional days of inpatient stay would likely benefit a patient, and if so, by how much.

A clinician may review the IRT score with the patient's score on a particular FIM item to determine whether additional interventions are appropriate. For example, if the patient has AQ score of 1, a score of 4 on the FIM toileting measure is expected. But, if the FIM toileting measure is lower, the clinician can use that as an indication to adjust therapy to specifically target improved toileting.

FIG. 6A and FIG. 6B are a "FIM Explorer" section, with features to allow clinicians to select and/or set the goal for each FIM-specific task. For instance, '4—Minimal Assistance' is chosen in FIG. 6A as a treatment goal for eating task. Once a task-specific goal is chosen, a comparison chart shown at FIG. 7 may be displayed. This chart can allow a therapist or other clinician to compare whether the goals are set too high or too low when compared with the vertical line on the chart. The vertical line is derived from the selected goal ratings and converted into an IRT score.

FIG. 8 displays various plots for the Self Care domain in comparison with a patient's FIM score. As shown in FIG. 8, the assessment areas within the Self Care domain include Balance, Upper Extremity Function, and Swallowing. In one embodiment, incomplete FIM administration may be omitted from the plot, to avoid confusion about whether the score is low or merely incomplete.

Prediction

Prediction of AQ score may be based on various factors, such as medical service group; case mix group (CMG); and/or lengths of stay. Within CMG, age may be a factor used to assist in the prediction.

Data generated by predictive models may be used in various ways. For example, a patient's length of stay can be predicted via his/her medical condition, level of impairment, and other demographic and clinical characteristics. As another example, if a patient is below their prediction on a given domain, clinicians can target those areas for more focused therapies. As another example, if a patient's progress in one domain has begun to taper off, clinicians could note this and prioritize balanced treatment in that domain. As another example, given some financial information, it would be possible to assess the dollar value of expected improvement over a period of time and compare it to the cost of inpatient care over that same time frame. Discharge decisions could be made using the ratio of value of care to cost of care. Additionally, predicting success in other treatment settings is possible. Given similar assessments in other levels and locations of care (e.g., outpatient, SNF, etc.), a prospective look at the course of improvement in those settings could be determined. Better decisions regarding care in those settings could potentially be made.

APPENDIX 1

| No. | Item | Instructions | Responses | Domain and Area/Cluster |
|---|---|---|---|---|
| 1 | Standing to Sitting | Please sit down. | 4) Sits safely with minimal use of hands<br>3) Controls descent by using hands<br>2) Uses back of legs against chair to control descent<br>1) Sits independently but has uncontrolled descent<br>0) Needs assistance to sit | Domain: Self Care<br>Area/Cluster: Balance<br>Domain: Mobility<br>Area/Cluster: Balance |
| 2 | Standing Unsupported with Feet Together | Place your feet together and stand without holding. | 4) Able to place feet together independently and stand for 1 minute safely<br>3) Able to place feet together independently and stand for 1 min with supervision<br>2) Able to place feet together independently and to hold for 30 seconds<br>1) Needs help to attain position but able to stand 15 seconds feet together | Domain: Self Care<br>Area/Cluster: Balance<br>Domain: Mobility<br>Area/Cluster: Balance |
| 3 | Reaching Forward with Outstretched Arm while Standing | Lift arm to 90 degrees. Stretch out your fingers and reach forward as far as you can. (Examiner places a ruler at end of fingertips when arm is at 90 degrees. Fingers should not touch the ruler while reaching forward. The recorded measure is the distance forward that the finger can reach while the subject is in the most forward lean position. When possible, ask subject to use both arms when reaching to avoid rotation of the trunk.) | 4) can reach forward confidently > 25 cm (10 inches)<br>3) can reach forward > 12.5 cm safely (5 inches)<br>2) can reach forward > 5 cm safely (2 inches)<br>1) reaches forward but needs supervision<br>0) loses balance while trying/requires external support | Domain: Self Care<br>Area/Cluster: Balance<br>Domain: Mobility<br>Area/Cluster: Balance |
| 4 | Pick Up Object From the Floor From a Standing Position | Pick up the shoe/slipper which is placed in front of your feet. May use an empty tissue box for testing instead of the shoe/slipper. | 4) able to pick up object safely and easily<br>3) able to pick up object but needs supervision<br>2) unable to pick up object but reaches 1-2 in. from object, keeps balance independently<br>1) unable to pick up and needs supervision while trying<br>0) unable to try/needs assist to keep from losing balance or falling | Domain: Self Care<br>Area/Cluster: Balance<br>Domain: Mobility<br>Area/Cluster: Balance |
| 5 | Turn 360 Degrees | Turn completely around in a full circle. Pause. Then turn a full circle in the other direction. | 4) able to turn 360 degrees safely in 4 seconds or less<br>3) able to turn 360 degrees safely one side only in 4 seconds or less<br>2) able to turn 360 degrees safely but slowly<br>1) needs close supervision or verbal cueing<br>0) needs assistance while turning | Domain: Self Care<br>Area/Cluster: Balance<br>Domain: Mobility<br>Area/Cluster: Balance |
| 6 | Anterior Nudge | Light anterior nudge to superior sternum | 4) Independent (completes task independently & successfully)<br>3) Verbal cues/increased time (completes task independently & successfully and only needs more time/cues)<br>2) Upper extremity support (must use UE for support or assistance to complete successfully)<br>1) Needs assistance (unable to complete without physical assist)<br>0) Dependent (requires complete physical assist, unable to complete successfully even with physical assist) | Domain: Self Care<br>Area/Cluster: Balance<br>Domain: Mobility<br>Area/Cluster: Balance |
| 7 | Static Sitting | Have patient sit for 30 seconds | | Domain: Self Care<br>Area/Cluster: Balance<br>Domain: Mobility<br>Area/Cluster: Balance |
| 8 | Sitting, Eyes Closed | Have patient sit with eyes closed for 30 seconds | | Domain: Self Care<br>Area/Cluster: Balance<br>Domain: Mobility<br>Area/Cluster: Balance |
| 9 | Sitting, Left Foot | Have patient sit, dominant side, lift foot 1 inch twice | | Domain: Self Care<br>Area/Cluster: Balance<br>Domain: Mobility<br>Area/Cluster: Balance |

APPENDIX 1-continued

| No. | Item | Instructions | Responses | Domain and Area/Cluster |
|---|---|---|---|---|
| 10 | Lateral Reach | Have patient use dominant arm, clear opposite ischial tuperosity | | Domain: Self Care<br>Area/Cluster: Balance<br>Domain: Mobility<br>Area/Cluster: Balance |
| 11 | Pick Up Object from Floor | Have patient pick up object from floor, from between feet | | Domain: Self Care<br>Area/Cluster: Balance<br>Domain: Mobility<br>Area/Cluster: Balance |
| 12 | Gait, Level Surface | Walk at your normal speed from here to the next mark (6 m [20 ft]). | 3) Normal: Walks 6 m (20 ft) in less than 5.5 seconds, no assistive devices, good speed, no evidence for imbalance, normal gait pattern, deviates no more than 15.24 cm (6 in) outside of the 30.48-cm (12-in) walkway width.<br>2) Mild impairment: Walks 6 m (20 ft) in less than 7 seconds but greater than 5.5 seconds, uses assistive device, slower speed, mild gait deviations, or deviates 15.24-25.4 cm (6-10 in) outside of the 30.48-cm (12-in) walkway width.<br>1) Moderate impairment-Walks 6 m (20 ft), slow speed, abnormal gait pattern, evidence for imbalance, or deviates 25.4-38.1 cm (10-15 in) outside of the 30.48-cm (12-in) walkway width. Requires more than 7 seconds to ambulate 6 m (20 ft).<br>0) Severe impairment-Cannot walk 6 m (20 ft) without assistance, severe gait deviations or imbalance, deviates greater than 38.1 cm (15 in) outside of the 30.48-cm (12-in) walkway width or reaches and touches the wall. | Domain: Self Care<br>Area/Cluster: Balance<br>Domain: Mobility<br>Area/Cluster: Balance |
| 13 | Gait with Vertical Head Turns | Walk from here to the next mark (6 m [20 ft]). Begin walking at your normal pace. Keep walking straight; after 3 steps, tip your head up and keep walking straight while looking up. After 3 more steps, tip your head down, keep walking straight while looking down. Continue alternating looking up and down every 3 steps until you have completed 2 repetitions in each direction. | 3) Normal-Performs head turns with no change in gait. Deviates no more than 15.24 cm (6 in) outside 30.48-cm (12-in) walkway width.<br>2) Mild impairment-Performs task with slight change in gait velocity (eg, minor disruption to smooth gait path), deviates 15.24-25.4 cm (6-10 in) outside 30.48-cm (12-in) walkway width or uses assistive device.<br>1) Moderate impairment-Performs task with moderate change in gait velocity, slows down, deviates 25.4-38.1 cm (10-15 in) outside 30.48-cm (12-in) walkway width but recovers, can continue to walk.<br>0) Severe impairment-Performs task with severe disruption of gait (eg, staggers 38.1 cm [15 in] outside 30.48-cm (12-in) walkway width, loses balance, stops, reaches for wall). | Domain: Self Care<br>Area/Cluster: Balance<br>Domain: Mobility<br>Area/Cluster: Balance |
| 14 | Gait and Pivot Turn | Instructions: Begin with walking at your normal pace. When I tell you, "turn and stop," turn as quickly as you can to face the opposite direction and stop. | 3) Normal-Pivot turns safely within 3 seconds and stops quickly with no loss of balance.<br>2) Mild impairment-Pivot turns safely in >3 seconds and stops with no loss of balance, or pivot turns safely within 3 seconds and stops with mild imbalance, requires small steps to catch balance.<br>1) Moderate impairment-Turns slowly, requires verbal cueing, or requires several small steps to catch balance following turn and stop.<br>0) Severe impairment-Cannot turn safely, requires assistance to turn and stop. | Domain: Self Care<br>Area/Cluster: Balance<br>Domain: Mobility<br>Area/Cluster: Balance |
| 15 | Step Over Obstacle | Begin with walking at your normal pace. When I tell you, "turn and stop," turn as quickly as you can to face the opposite direction and stop. | 3) Normal-Is able to step over 2 stacked shoe boxes taped together (22.86 cm [9 in] total height) without changing gait speed; no evidence of imbalance.<br>2) Mild impairment-Is able to step over one shoe box (11.43 cm [4.5 in] total height) without changing gait speed; no evidence of imbalance.<br>1) Moderate impairment-Is able to step over one shoe box (11.43 cm [4.5 in] total height) but must slow down and adjust steps to clear box safely. May require verbal cueing.<br>0) Severe impairment-Cannot perform without assistance. | Domain: Self Care<br>Area/Cluster: Balance<br>Domain: Mobility<br>Area/Cluster: Balance |
| 16 | Ambulating Backwards | Walk backwards until I tell you to stop. | 3) Normal-Walks 6 m (20 ft), no assistive devices, good speed, no evidence for imbalance, normal gait pattern, deviates no more than 15.24 cm (6 in) outside 30.48-cm (12-in) walkway width.<br>2) Mild impairment-Walks 6 m (20 ft), uses assistive device, slower speed, mild gait deviations, deviates 15.24-25.4 cm (6-10 in) outside 30.48-cm (12-in) walkway width.<br>1) Moderate impairment-Walks 6 m (20 ft), slow speed, abnormal gait pattern, evidence for imbalance, deviates 25.4-38.1 cm (10-15 in) outside 30.48-cm (12-in) walkway width. | Domain: Self Care<br>Area/Cluster: Balance<br>Domain: Mobility<br>Area/Cluster: Balance |

APPENDIX 1-continued

| No. | Item | Instructions | Responses | Domain and Area/Cluster |
|---|---|---|---|---|
| | | | 0) Severe impairment-Cannot walk 6 m (20 ft) without assistance, severe gait deviations or imbalance, deviates greater than 38.1 cm (15 in) outside 30.48-cm (12-in) walkway width or will not attempt task. | |
| 17 | Grasp | Pickup 2.5 cm block | 3 = task is completed in less than 5 seconds; appropriate body posture; normal hand movement components; normal arm movement components | Domain: Self Care Area/Cluster: Upper Extremity Function |
| 18 | Grip | Pour water from one glass to another | 2 = task is completed but either with great difficulty or takes abnormally long. "Great difficulty" means abnormal hand movement components (i.e. wrong grasp), abnormal | Domain: Self Care Area/Cluster: Upper Extremity Function |
| 19 | Pinch | Grasp the ball bearing (or marble) using these fingers, lift it up, and place it in the tin on top of the shelf. Patient attempts to lift the (6 mm) ball bearing (or marble) with $3^{rd}$ finger and thumb | arm movements (i.e. elbow does not flex as required), or abnormal body movements (i.e. trunk compensations), "abnormally long" means between 5-60 seconds. 1 = Patient only partially completes the task within the 60 seconds, regardless of hand/arm movements patterns or postural requirements. For grasp, grip and pinch | Domain: Self Care Area/Cluster: Upper Extremity Function |
| 20 | Hand to mouth | Touch your mouth with the palm of your hand. | subscales, score is not attainable without some form of hand movement. Simply pushing the object across table does not = 1. 0 = Given when the patient is unable to complete any part of the hand or arm movement within 60 seconds. | Domain: Self Care Area/Cluster: Upper Extremity Function |
| 21 | Dexterity | I want to see how quickly you can pick up one block at a time with your right (or left) hand. Carry it to the other side of the box and drop it. Make sure your fingertips cross the partition. | | Domain: Self Care Area/Cluster: Upper Extremity Function |
| 22 | Peg Test | "Pick up the pegs one at a time, using one hand only, and put them in the holes as quickly as possible. You can do them in any order until all of the holes are filled. Then, without pausing, remove the pegs one at a time and return them to the container as quickly as you can. We will do this two times with each hand." | | Domain: Self Care Area/Cluster: Upper Extremity Function |
| 23 | Functional Oral Intake Scale | | | Domain: Self Care Area/Cluster: Swallowing |
| 24 | Saliva | Observe the patient's control of saliva. Note any escape of secretions from the side of the mouth, and check corners of mouth for wetness. Ask the patient if he or she has noticed undue saliva loss during the day, at night, or while side lying. | 5) NAD 4) frothy/expectorated 3) drooling at times 2) some drool consistently 1) gross drool | Domain: Self Care Area/Cluster: Swallowing |
| 25 | Tongue Movement | Anterior Aspect: Protrusion - have patient extend tongue as far forward as possible and then retract similarly. Lateralization - have patient touch each corner of the mouth, then repeat alternating lateral movements. With tongue, have patient attempt to clear out lateral sulci on each side of the mouth. Elevation - With mouth open wide, have patient raise tongue tip to alveolar ridge. Alternate elevation and depression in this way. Posterior Aspect: Elevation - have patient raise back of tongue to meet palate and hold the position | 10) full range of motion ("ROM") 8) mild impairment in range 6) incomplete movement 4) minimal movement 2) no movement | Domain: Self Care Area/Cluster: Swallowing |
| 26 | Tongue Strength | Have patient push laterally, against a tongue depressor or gloved finger. Have patient push anteriorly, against a tongue depressor or gloved finger. Have patient push during elevation and depression of the tongue. Ask patient to elevate back of tongue against a tongue depressor or gloved finger. Note tone and strength to resistance. | 10) NAD 8) minimal weakness 5) unilateral weakness 2) gross weakness | Domain: Self Care Area/Cluster: Swallowing |

APPENDIX 1-continued

| No. | Item | Instructions | Responses | Domain and Area/Cluster |
|---|---|---|---|---|
| 27 | Tongue Coordination | Ask patient to lick around lips, slowly and then rapidly, touching all parts. Have patient rapidly repeat tongue ripe alveolar syllables /ta/. Repeat a sentence including tongue tip alveolar consonants e.g. Take Tim to tea). Ask patient to rapidly repeat velar syllables /ka/. Repeat a sentence including velar consonants e.g., Can you keep Katie clean?). | 10) NAD 8) mild incoordination 5) gross incoordination 2) no movement unable to assess | Domain: Self Care Area/Cluster: Swallowing |
| 28 | Oral Preparation | Observe patient while eating or chewing. Ask to observe how bolus is prepared prior to swallowing. Check for loss from mouth, position of food bolus, spread throughout oral cavity, and loss of material into lateral or anterior sulci. Note chewing movements and fatigue. | 10) NAD 8) lip or tongue seal bolus escape 6) minimal chew thrust gravity assisted 4) no bolus formation no attempt 2) unable to examine | Domain: Self Care Area/Cluster: Swallowing |
| 29 | Bolus Clearance | Observe patient eating/swallowing a bolus. Check oral cavity for residue following a swallow. | 10) fully cleared 8) significant clearance/minimal residue 5) some clearance/residue 2) no clearance | Domain: Self Care Area/Cluster: Swallowing |
| 30 | Oral Transit | The clinician will position a hand under the patient's chin, with fingers spread as per manual palpation method Logemann, 1983). Use only a light touch. Ask the patient to swallow. Compare time elapsed between the initiation of lingual movement until the initiation of hyoid and laryngeal rise. | 10) NAD, triggers rapidly within 1 second 8) delay > 1 sec 6) delay > 5 sec 4) delay > 4 sec 2) no movement observed | Domain: Self Care Area/Cluster: Swallowing |
| 31 | Voluntary Cough | Ask the patient to cough as strongly as possible. Observe strength and clarity of cough. | 10) NAD, strong clear cough 8) attempt bovine 5) attempt inadequate 2) no attempt/unable to assess | Domain: Self Care Area/Cluster: Swallowing |
| 32 | Pharyngeal Phase | Observe hyoid and laryngeal movement using manual palpation method Logemann, 1983). Note smoothness of excursion and maximal elevation point. Following swallow, ask patient to phonate/ah/ for several seconds. Note vocal quality. Ask patient to pant following swallow then vocalize. Note vocal quality Ask patient to turn head to each side and vocalize. Note vocal quality. Ask patient to lift chin and vocalize. Note vocal quality. | 10) immediate laryngeal elevation clearance of material 8) laryngeal elevation mildly restricted slow initiation incomplete clearance 5) pooling/gurgling laryngeal elevation incomplete 2) no swallow unable to assess | Domain: Self Care Area/Cluster: Swallowing |
| 33 | Pharyngeal Response | Observe vocal quality and coughing as a result of swallow. To be completed in association with other assessment tasks. | 10) NAD 5) cough before/during/after swallow 1) not coping/gurgling | Domain: Self Care Area/Cluster: Swallowing |
| 34 | RIC Dysphagia Supervision Scale | Dysphagia supervision instructions. | 6) No cueing needed to safely tolerate diet. Independent. 5) Needs cues 10% of the time to safely tolerate diet. Standby prompting. 4) Needs cues 10-25% of the time to safely tolerate diet. Minimal cues. 3) Needs cues 25-50% of the time to safely tolerate diet. Moderate cues. 2) Needs cues 50-75% of the time to safely tolerate diet. Maximal cues. 1) Needs cues 75-100% of the time to safely tolerate diet. Total assistance. 0) For NPO patients and patients who are physically dependent for eating. | Domain: Self Care Area/Cluster: Swallowing |
| 35 | Pressure Relief | Pressure relief instructions | | Domain: Mobility Area/Cluster: Wheelchair Skills |
| 36 | 5 Time Sit to Stand | Patient sits with arms folded across chest and with their back against a chair. For patients with history of stroke, it is acceptable to have the impaired arm at their side or in a sling. Use a chair at height from | Record amount of time required to complete the test. Timing begins at "Go" and stops when the patient's buttocks touch the chair on the fifth repetition. | Domain: Mobility Area/Cluster: Changing Body Positions Domain: Mobility Area/Cluster: Mobility |

APPENDIX 1-continued

| No. | Item | Instructions | Responses | Domain and Area/Cluster |
|---|---|---|---|---|
| | | 43-45 cm. Ensure that the chair is not secured (i.e against the wall or mat). Instructions: "I want you to stand up and sit down 5 times as quickly as you can when I say 'Go'." Instruct to stand fully between repetitions of the test and not to touch the back of the chair during each repetition. | | |
| 37 | Bed Mobility (Prone) | | | Domain: Mobility Area/Cluster: Changing Body Positions Domain: Mobility Area/Cluster: Bed Mobility |
| 38 | Short Sit to Bed/Mat (Supine) | | | Domain: Mobility Area/Cluster: Bed Mobility |
| 39 | Supine to long sit/ring sit | | | Domain: Mobility Area/Cluster: Bed Mobility |
| 40 | Self ROM | | | Domain: Mobility Area/Cluster: Bed Mobility |
| 41 | Timed Stair Climb | | | Domain: Mobility Area/Cluster: Mobility |
| 42 | 6 Minute Walk | | | Domain: Mobility Area/Cluster: Mobility |
| 43 | Borgs RPE | | | Domain: Mobility Area/Cluster: Mobility |
| 44 | 10 Meter Walk Test | | | Domain: Mobility Area/Cluster: Mobility |
| 45 | 6 Minute Push | | | Domain: Mobility Area/Cluster: Mobility |
| 46 | City | Patient should name the city they are currently in | 3: Correct Spontaneous or upon first free recall attempt 2: Correct upon logical cueing (i.e. that was yesterday, so today . . .) 1: Correct upon multiple choice or phonemic cueing 0: incorrect despite cueing, inappropriate response or unable to respond. | Domain: Cognition Area/Cluster: Cognition |
| 47 | Name of Hospital | Patient should name the hospital they are currently at | | Domain: Cognition Area/Cluster: Cognition |
| 48 | Month | Patient should know the current month | | Domain: Cognition Area/Cluster: Cognition |
| 49 | Year | Patient should know the current year | | Domain: Cognition Area/Cluster: Cognition |
| 50 | Clock Time | Patient should know the time, may be +/−30 minutes. They can look at a clock without penalty | | Domain: Cognition Area/Cluster: Cognition |
| 51 | Etiology/Event | Patient should know what brought them into the hospital (i.e. what brought you in today?) | | Domain: Cognition Area/Cluster: Cognition |
| 52 | Gaze Orientation | No instructions to the patient. Instructions to clinician: observe patient gaze. | 3: The patient is easily able to direct his gaze toward the right side of the space but does not attempt to orient the eyes toward the left side. 2: There are constant and clear asymmetries in the gaze direction toward the left and right sides of space. The patient explores the environment by looking toward the right first, and after a long delay, slowly looks toward the left. During the entire session, the patient spends much more time looking to his right side. 1: There are inconsistent but observable asymmetries in the gaze direction toward the left and right sides of space. The patient explores an environment by looking toward the right first, and then slowly toward the left with some hesitation. During the entire session the patient looks toward the right more than the left. 0: The patient spontaneously directs his/her gaze toward the right and left sides of space without hesitation and without any prompting. | Domain: Cognition Area/Cluster: Cognition |
| 53 | Limb Awareness | No instructions to patient. Instructions to clinician: observe patient use of limbs. | 3: The patient completely ignores the left limbs and never attempts, with the assistance of the right hand, to move the left arm or and leg, or verbally acknowledge any discomfort in the left arm and leg. You cannot observe any spontaneous caring for the left limbs. 2: Time spent caring for the left limbs is short with incomplete performance. For example, during the entire session, they care for their left arm once, by moving it over to the arm rest, but for the remainder of the session they do not care much for it and let it accidentally hang outside the chair. Another example, is when asked to wash their hands, they do not wash their left hand or only | Domain: Cognition Area/Cluster: Cognition |

APPENDIX 1-continued

| No. | Item | Instructions | Responses | Domain and Area/Cluster |
|---|---|---|---|---|
| | | | wash it incidentally. Or you may think of the entire session in a continuous time period. If the patient takes care of their left limb only ⅓ of the time, give them a score of 2.<br>1: If the patient takes care of their left limbs ⅔ of the time, you give them a score of 1.<br>0: The patient pays attention and cares for their left limbs or as much as they do for their right limbs. Even if they complain of difficulty moving the left limbs or ask for help, because it means they pay attention to the left limbs. | |
| 54 | Auditory Attention | No instructions to patient. Instructions to clinician: Make sure you are out of the patient's sightlines, and then without warning, make a loud noise to the patients right or left side. You can drop an object or clap loudly. Do it once on the left side, and once to the right side later. Observe whether patient has an immediate reaction like startle, blinking, or wincing. | 3: The patient shows an immediate reaction to the sound from the right side but no reaction from the left side at all.<br>2: The patient shows immediate reaction to the sound from the right side, but the reaction from the left side is inadequate or incorrect. For example, the patient may state they heard something but is not able to identify the location or the noise. They shift their head or body to the opposite side from which the noise is actually coming.<br>1: The patient immediately reacts to the sound from the right correctly but takes an observably longer time or hesitates to the sound from the left.<br>0: All the reactions observed are correct and immediate on both left and right sides. | Domain: Cognition<br>Area/Cluster: Cognition |
| 55 | Personal Belongings | Ask patient for the location of 3 personal belongings on the patient's right and 3 on the patient's left. To be considered a personal belonging the item must almost always be kept at a certain location by the patient. Do not hide or arrange the objects for the patient to find, preferred locations should be determined by the patient. In asking for the object location, phrase the question "I can't find x, can you tell me where it is?". Observe how the patient looks around to locate the object and explore their environment | 3: The patient always locates and points to objects on their right side by fails to locate any objects on the left side.<br>2: The patient always locates and points to objects on their right side but fails to locate ⅔ of the objects on the left side.<br>1: The patient always locates and points to the objects on their right side but fails to locate and point to ⅓ of the objects on the left side.<br>0: The patients does not hesitate to locate and point to objects on the right and left side. | Domain: Cognition<br>Area/Cluster: Cognition |
| 56 | Dressing | Ask patient to put on an open front shirt or coat. Look for differences in performance on the left and right sides of the body. | 3: The patient only attempts to dress the right arm and completely ignores the left, making no attempt to put the left arm through the sleeve, and odes not acknowledge a need for help.<br>2: The patient does not acknowledge a need for help. They start by putting their right arm in the sleeve and continue the left arm. However, they spend significantly less time in dressing their left arm, and the shirt is very messy on the left side. In the end the performance on the left is incomplete and ineffective.<br>1: The patient does not acknowledge the need for help. They may first attend to their right side, putting their right arm in the sleeve and eventually with some hesitation, work the left arm into its sleeve as well. In the end, the patient is able to put on the shirt, but the left side is not completely pulled down or does not appear as nicely as the right side. The patient does not acknowledge a need for help.<br>0: The patient asks for help with the left side of the body, and is paying attention to his/her left arm by trying hard to complete the task on the left side. Assessment measures awareness of disability and so a 0 may be given to a patient who cannot complete the task but asks for help as it indicates they are not neglecting the left arm. | Domain: Cognition<br>Area/Cluster: Cognition |
| 57 | Grooming | Ask the patient to perform 3 grooming tasks. | 3: In all three tasks, the patient only pays attention to the right and always ignores the left side.<br>2: The patient always takes care of the right side first, and miss the left side in at least one of the tasks.<br>1: The patient completes all three tasks in a satisfactory manner. They always take care of the right side first, and spend significantly shorter time and put in less effort on the left side.<br>0: The patient completes all three tasks with no apparent left side asymmetry. | Domain: Cognition<br>Area/Cluster: Cognition |
| 58 | Distraction | Observe the patient for short attention span, easy distractibility, and inability to concentrate. | 1 = absent: the behavior is not present.<br>2 = present to a slight degree: the behavior is present but does not prevent | Domain: Cognition<br>Area/Cluster: Cognition |

APPENDIX 1-continued

| No. | Item | Instructions | Responses | Domain and Area/Cluster |
|---|---|---|---|---|
| 59 | Impulsiveness | Observe the patient for indications of impulsiveness, impatience, and low tolerance for pain or frustration. | the conduct of other, contextually appropriate behavior. (The individual may redirect spontaneously, or the continuation of the agitated behavior does not disrupt appropriate behavior.) 3 = present to a moderate degree: the individual needs to be redirected from an agitated to an appropriate behavior, but benefits from such cueing. 4 = present to an extreme degree: the individual is not able to engage in appropriate behavior due to the interference of the agitated behavior, even when external cueing or redirection is provided. | Domain: Cognition Area/Cluster: Cognition |
| 60 | Cooperation | Observe the patient for uncooperative behavior, resistance to care, and demanding behavior. | | Domain: Cognition Area/Cluster: Cognition |
| 61 | Pulling | Observe the patient for pulling at tubes, restraints, etc. | | Domain: Cognition Area/Cluster: Cognition |
| 62 | Repetition | Observe the patient for repetitive behaviors, motor and/or verbal. | | Domain: Cognition Area/Cluster: Cognition |
| 63 | Behavioral Observation Profile | | | Domain: Cognition Area/Cluster: Cognition |
| 64 | Pragmatic Communication Skills | | | Domain: Cognition Area/Cluster: Cognition |
| 65 | Delayed Recall 3 Words | | | Domain: Cognition Area/Cluster: Memory |
| 66 | Rivermead Immediate Story Retell | | | Domain: Cognition Area/Cluster: Memory |
| 67 | Rivermead Delayed Story Retell | | | Domain: Cognition Area/Cluster: Memory |
| 68 | Basic word description | | | Domain: Cognition Area/Cluster: Communication |
| 69 | Commands | | | Domain: Cognition Area/Cluster: Communication |
| 70 | Complex Ideation | | | Domain: Cognition Area/Cluster: Communication |
| 71 | Word repetition | | | Domain: Cognition Area/Cluster: Communication |
| 72 | Sentence repetition | | | Domain: Cognition Area/Cluster: Communication |
| 73 | Form | | | Domain: Cognition Area/Cluster: Communication |
| 74 | Letter choice | | | Domain: Cognition Area/Cluster: Communication |
| 75 | Motor facility | | | Domain: Cognition Area/Cluster: Communication |
| 76 | Picture-word matching | | | Domain: Cognition Area/Cluster: Communication |
| 77 | Oral word reading | | | Domain: Cognition Area/Cluster: Communication |
| 78 | Oral sentence reading | | | Domain: Cognition Area/Cluster: Communication |
| 79 | Sentence/paragraph comprehension | | | Domain: Cognition Area/Cluster: Communication |
| 80 | Boston Naming Test | | | Domain: Cognition Area/Cluster: Communication |

What is claimed is:

1. A computer-assisted method for assessing a patient, comprising a computing device carrying out actions comprising:

a. using item response theory (IRT), pre-selecting tasks for a plurality of assessments for assessing the patient in a plurality of domains;

b. receiving an input of a first assessment, among the plurality of assessments, the first assessment having a plurality of tasks in a self-care domain with items in the areas of balance, upper extremity function, and swallowing;

c. receiving an input of a second assessment, among the plurality of assessments, the second assessment having a plurality of tasks in a mobility domain with items in the areas of balance, wheelchair skills, changing body positions, bed mobility, and mobility;
d. receiving an input of a third assessment, among the plurality of assessments, the third assessment having a plurality of tasks in a cognition domain with items in the areas of cognition, memory, and communication;
e. generating a plurality of respective domain-specific IRT scores based on patient performance on respective pluralities of tasks in respective ones of the received assessments, the plurality of respective domain-specific IRT scores being generated at least by applying IRT analysis based on statistical models generated for respective ones of the plurality of domains, the respective statistical models being from among respective pluralities of statistical models corresponding to respective ones of the plurality of domains, to respective ones of the received assessments, including generating i) a self-care IRT score based on patient performance on the plurality of tasks in the first assessment, ii) a mobility IRT score based on patient performance on the plurality of tasks in the second assessment and iii) a cognition IRT score based on patient performance on the plurality tasks in the third assessment; and
f. storing the generated domain-specific IRT scores in an electronic medical record.

2. The method of claim 1, further comprising:
retrieving the domain-specific IRT scores from the electronic medical record; and
adjusting a treatment plan based on the retrieved domain-specific IRT scores.

3. The method of claim 1, further comprising applying factor analysis to data derived from the electronic medical record.

4. The method of claim 1, further comprising applying classical item analysis data derived from the electronic medical record.

5. A method of measuring improvements in a rehabilitation patient, comprising a computing device carrying out actions comprising:
a. using item response theory (IRT) analysis based on a plurality of statistical models generated for a plurality of assessment domains, pre-selecting a plurality of assessments for assessing the rehabilitation patient in respective ones of the plurality of assessment domains;
b. receiving an input of an assessment of the plurality relating to self-care;
c. receiving an input of an assessment of the plurality relating to mobility;
d. receiving an input of an assessment of the plurality relating to cognition;
e. storing the received inputs in an electronic medical record;
f. determining, based on at least one of the plurality of assessments, at least one score to measure an improvement of the rehabilitation patient in at least one of the plurality of domains; and
g. comparing the score against a predicted score for the rehabilitation patient in the at least one of the plurality of domains, the predicted score based at least in part on a severity of diagnoses associated with the rehabilitation patient in the at least one of the plurality of domains, wherein the comparison is used to improve a therapy in the at least one of the plurality of domains.

6. The method of claim 5, wherein the plurality of assessments are further selected using factor analysis.

7. The method of claim 6, wherein the plurality of assessments are further selected using classical item analysis.

8. The method of claim 5, wherein the each of the self-care, mobility, and cognition assessments is broken into factors.

9. The method of claim 8, wherein the factors for self-care are balance, upper extremity function, and swallowing.

10. The method of claim 5, further comprising the computing device displaying the at least one score on a display screen.

11. The method of claim 5, wherein the comparison is used to i) identify an area of therapeutic need and ii) target the therapy to the area of therapeutic need.

12. The method of claim 5, wherein
determining at least one score to measure an improvement of the rehabilitation patient in at least one of the plurality of domains comprises determining a plurality of scores to measure respective improvements of the rehabilitation patient in the plurality of domains; and
comparing the respective scores against respective predicted scores for the rehabilitation patient in the plurality of domains, the respective predicted scores based at least in part on respective severities of diagnoses associated with the rehabilitation patient in respective ones of the plurality of domains.

13. The method of claim 12, wherein the comparisons are used to identify one or more particular domains, among the plurality of domains, in which the rehabilitation patient has made improvement.

14. The method of claim 12, wherein the comparisons are used to identify one or more particular domains, among the plurality of domains, in which additional therapy is needed for the rehabilitation patient.

15. A computer-assisted method for assessing a patient, comprising a computing device carrying out actions comprising:
a. using item response theory (IRT) analysis based on respective statistical models, among a plurality of statistical models generated for a plurality of domains, pre-selecting tasks for respective assessment among a plurality of assessments for assessing the patient in respective domains among the plurality of domains, wherein at least one statistical model among the plurality of statistical models is a multigroup statistical model based on a sample of patients, the sample of patients comprising a plurality of groups of patients grouped according to categories indicative of abilities of the patients in a particular domain among the plurality of domains;
b. receiving an input of a first assessment, among the plurality of assessments, the first assessment having a plurality of tasks in a self-care domain with items in the areas of balance, upper extremity function, and swallowing;
c. receiving an input of a second assessment, among the plurality of assessments, the second assessment having a plurality of tasks in a mobility domain with items in the areas of balance, wheelchair skills, changing body positions, bed mobility, and mobility;
d. receiving an input of a third assessment, the third assessment having a plurality of tasks in a cognition domain with items in the areas of cognition, memory, and communication;
e. generating, at least by applying IRT analysis based on respective ones of the statistical models to corresponding ones of the received assessments, respective domain-specific IRT scores based on patient performance on respective pluralities of tasks in respective ones of the received assessments, including generating i) a self-care IRT score based on patient performance on the plurality of tasks in the first assessment, ii) a mobility IRT score based on patient performance on the plurality of tasks in the second assessment and iii) a cognition IRT score based on patient performance on the plurality tasks in the third assessment; and f. storing the generated domain-specific IRT scores in an electronic medical record.

16. The method of claim 15, wherein the multigroup statistical model i) is for assessing the patient in one of the self-care domain and the mobility domain and ii) is based on a plurality of groups of patients grouped according to categories indicative of levels of balance of the patients.

17. The method of claim 16, wherein the levels of balance of the patients include two or more of i) no balance, ii) sitting balance, iii) standing balance and iv) walking balance.

18. The method of claim 15, wherein the multigroup statistical model i) is for assessing the patient in the cognition domain and ii) is based on a plurality of groups of patients grouped according to cognitive diagnoses of the patients.

19. The method of claim 18, wherein the cognitive diagnoses of the patients include two or more of i) normal cognition, ii) stroke, iii) brain injury and iv) neurological abnormality.

20. The method of claim 12, wherein the multigroup statistical model based on a plurality of groups of patients grouped according to categories indicative of abilities of the patients in a particular domain ensures that an item is excluded from the corresponding assessment if the item is not appropriate for ability of the patient in the particular domain.

* * * * *